US012053161B2

(12) United States Patent
Yabe

(10) Patent No.: US 12,053,161 B2
(45) Date of Patent: Aug. 6, 2024

(54) ENDOSCOPE APPARATUS, INFORMATION STORAGE MEDIUM, CONTROL METHOD OF ENDOSCOPE APPARATUS, AND PROCESSING DEVICE

(71) Applicant: OLYMPUS CORPORATION, Tokyo (JP)

(72) Inventor: Yusuke Yabe, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 250 days.

(21) Appl. No.: 17/407,688

(22) Filed: Aug. 20, 2021

(65) Prior Publication Data
US 2021/0385367 A1 Dec. 9, 2021

Related U.S. Application Data

(63) Continuation of application No. PCT/JP2019/007270, filed on Feb. 26, 2019.

(51) Int. Cl.
*A61B 1/06* (2006.01)
*A61B 1/00* (2006.01)
(Continued)

(52) U.S. Cl.
CPC ...... *A61B 1/0638* (2013.01); *A61B 1/000094* (2022.02); *A61B 1/000096* (2022.02);
(Continued)

(58) Field of Classification Search
CPC ............ A61B 1/0638; A61B 1/000094; A61B 1/000096; A61B 1/0005; A61B 1/0655;
(Continued)

(56) References Cited

U.S. PATENT DOCUMENTS

2003/0139650 A1 7/2003 Homma
2010/0056928 A1* 3/2010 Zuzak .................. G01J 3/2823
356/302
(Continued)

FOREIGN PATENT DOCUMENTS

CN 108615037 A 10/2018
JP 2003-215469 A 7/2003
(Continued)

OTHER PUBLICATIONS

Japanese Office Action dated Apr. 19, 2022 received in 2021-501424.
International Search Report dated May 28, 2019 received in PCT/JP2019/007270.
(Continued)

*Primary Examiner* — Nasim N Nirjhar
(74) *Attorney, Agent, or Firm* — Scully, Scott, Murphy & Presser, P.C.

(57) ABSTRACT

An endoscope apparatus includes an illuminating device and a processor. The illuminating device emits display illumination light and support illumination light in a time-division manner. The processor generates a display image based on an image signal acquired when the display illumination light is emitted, and support information based on an image signal acquired when the support illumination light is emitted. The processor generates first support information when an illumination property is a first illumination property, superimposes first display content based on the first support information on the display image, switches the illumination property of the support illumination light to a second illumination property upon determination that the first support information satisfies a predetermined condition, generates second support information when the illumination property is the second illumination property, and superimposes second display content based on the second support information on the display image.

13 Claims, 15 Drawing Sheets

(51) Int. Cl.
  *A61B 5/00* (2006.01)
  *A61B 5/02* (2006.01)
  *A61B 5/107* (2006.01)
  *H04N 23/50* (2023.01)
  *H04N 23/56* (2023.01)
  *H04N 23/74* (2023.01)

(52) U.S. Cl.
  CPC .......... *A61B 1/0005* (2013.01); *A61B 1/0655* (2022.02); *A61B 5/02042* (2013.01); *A61B 5/1076* (2013.01); *A61B 5/489* (2013.01); *A61B 5/7267* (2013.01); *H04N 23/56* (2023.01); *H04N 23/74* (2023.01); *H04N 23/555* (2023.01)

(58) Field of Classification Search
  CPC ... A61B 5/02042; A61B 5/1076; A61B 5/489; A61B 5/7267; A61B 5/7264; A61B 2505/05; A61B 5/0075; H04N 23/56; H04N 23/74; H04N 23/555; G16H 30/40; G16H 40/67; G16H 50/20
  See application file for complete search history.

(56) References Cited

U.S. PATENT DOCUMENTS

| | | |
|---|---|---|
| 2017/0086659 A1 | 3/2017 | Uchiyama et al. |
| 2017/0231553 A1* | 8/2017 | Igarashi ................. A61B 18/00 600/479 |
| 2017/0265733 A1* | 9/2017 | Yabe ........................ A61B 1/00 |
| 2019/0365200 A1 | 12/2019 | Tatsuta et al. |
| 2021/0166385 A1* | 6/2021 | Shang ................... G06T 7/0012 |

FOREIGN PATENT DOCUMENTS

| | | |
|---|---|---|
| JP | 2006-181387 A | 7/2006 |
| JP | 2012-000160 A | 1/2012 |
| JP | 2012-010981 A | 1/2012 |
| JP | 2012-152333 A | 8/2012 |
| WO | 2016/084504 A1 | 6/2016 |
| WO | 2018/180250 A1 | 10/2018 |

OTHER PUBLICATIONS

Chinese Office Actin dated Dec. 23, 2023 received in 201980092951. 7.

* cited by examiner

ENDOSCOPE APPARATUS, INFORMATION STORAGE MEDIUM, CONTROL METHOD OF ENDOSCOPE APPARATUS, AND PROCESSING DEVICE

CROSS REFERENCE TO RELATED APPLICATION

This application is a continuation of International Patent Application No. PCT/JP2019/007270, having an international filing date of Feb. 26, 2019, which designated the United States, the entirety of which is incorporated herein by reference.

BACKGROUND

Application of AI technology has been considered in a field of endoscopes for medical use. For example, an AI technology is used to extract observation support information useful for detection or diagnosis of a lesion so as to display the observation support information on an endoscope monitor. Such a technique is disclosed by WO 2016/084504, for example. According to WO 2016/084504, when a diagnosis support mode is set to ON in a fluorescence observation mode, status of fluorescence in a criterion region and a target region is visualized to be displayed on a monitor, and diagnosis support is performed based on a change with time in the status displayed on the monitor.

Furthermore, there has been a known technique for controlling an illumination source to capture an image suitable for a purpose in an endoscope apparatus. Such a technique is disclosed by Japanese Unexamined Patent Application Publication Nos. 2006-181387 and 2003-215469, for example. According to Japanese Unexamined Patent Application Publication No. 2006-181387, a light distribution angle of illumination light is changed by a liquid crystal lens so as to decrease an error in acquiring biofunction information such as an oxygen saturation level. According to Japanese Unexamined Patent Application Publication No. 2003-215469, a spectral transmittance distribution is provided near a pupil of an imaging optical system such that an area of the pupil is increased with respect to light in a wavelength band desired to be enhanced out of return light from an object. As a result, desired deep tissue information can be observed in good contrast.

SUMMARY

In accordance with one of some aspect, there is provided an endoscope apparatus comprising:
  an illuminating device configured to change an illumination property of illumination light to emit display illumination light and support illumination light; and
  a processor configured to generate a display image based on an image signal acquired when the display illumination light is emitted, and support information based on an image signal acquired when the support illumination light is emitted, wherein
  the illuminating device emits the display illumination light and the support illumination light in a time-division manner, and
  the processor
    generates first support information based on the image signal when the illumination property is a first illumination property,
    superimposes first display content based on the first support information on the display image,
    switches the illumination property of the support illumination light from the first illumination property to a second illumination property upon determination that the first support information satisfies a predetermined condition,
    generates second support information based on the image signal when the illumination property is the second illumination property, and
    superimposes second display content based on the second support information on the display image.

In accordance with one of some aspect, there is provided a non-transitory information storage medium configured to store a program that causes a computer to perform steps of:
  emitting display illumination light and support illumination light in a time-division manner from an illuminating device;
  generating a display image based on an image signal acquired when the display illumination light is emitted:
  generating first support information based on an image signal when an illumination property of the support illumination light is a first illumination property;
  superimposing first display content based on the first support information on the display image:
  switching the illumination property of the support illumination light from the first illumination property to a second illumination property upon determination that the first support information satisfies a predetermined condition:
  generating second support information based on an image signal when the illumination property is the second illumination property; and
  superimposing second display content based on the second support information on the display image.

In accordance with one of some aspect, there is provided a control method of an endoscope apparatus, the method comprising:
  a step where an illuminating device emits display illumination light and support illumination light in a time-division manner;
  a step where a processor generates a display image based on an image signal acquired when the display illumination light is emitted:
  a step where the processor generates first support information based on an image signal when an illumination property of the support illumination light is a first illumination property:
  a step where the processor superimposes first display content based on the first support information on the display image;
  a step where the processor switches the illumination property of the support illumination light from the first illumination property to a second illumination property upon determination that the first support information satisfies a predetermined condition;
  a step where the processor generates second support information based on an image signal when the illumination property is the second illumination property; and
  a step where the processor superimposes second display content based on the second support information on the display image.

In accordance with one of some aspect, there is provided a processing device comprising a processor configured to perform:
  controlling an illumination source to switch illumination light between display illumination light and support illumination light in a time-division manner;

generating a display image from an image signal acquired based on the illumination light:

generating support information on diagnosis or treatment relating to an object to be examined from an image signal;

generating first support information based on an image signal acquired when the support illumination light has a first illumination property;

generating second support information based on an image signal acquired when the support illumination light has a second illumination property:

switching the support illumination light from the first illumination property to the second illumination property when the first support information satisfies a predetermined condition; and superimposing image information based on at least one of the first support information and the second support information on the display image.

In accordance with one of some aspect, there is provided a processing device comprising:

an illumination source control circuit configured to control an illumination source to switch illumination light between display illumination light and support illumination light in a time-division manner;

an image processing circuit configured to generate a display image from an image signal acquired based on the illumination light; and a support information generation circuit configured to generate support information on diagnosis or treatment relating to an object to be examined from an image signal, wherein the support information generation circuit generates first support information based on an image signal acquired when the support illumination light has a first illumination property, and generates second support information based on an image signal acquired when the support illumination light has a second illumination property, the illumination source control circuit switches the support illumination light from the first illumination property to the second illumination property when the first support information satisfies a predetermined condition, and the image processing circuit superimposes image information based on at least one of the first support information and the second support information on the display image.

In accordance with one of some aspect, there is provided a processing device comprising a controller configured to perform:

generating first information about an object to be examined from an image signal acquired using light having a first property;

generating second information about the object to be examined from an image signal acquired using light having a second property, the second information differing from the first information;

generating a display image from an image signal acquired using light having a third property;

superimposing image information based on at least one of the first information and the second information on the display image; and controlling an illumination source to emit the light having the second property and the light having the third property in a time-division manner, when the first information becomes predetermined status while the light having the first property and the light having the third property are emitted in a time-division manner.

DESCRIPTION OF EXEMPLARY EMBODIMENTS

Figure 1:
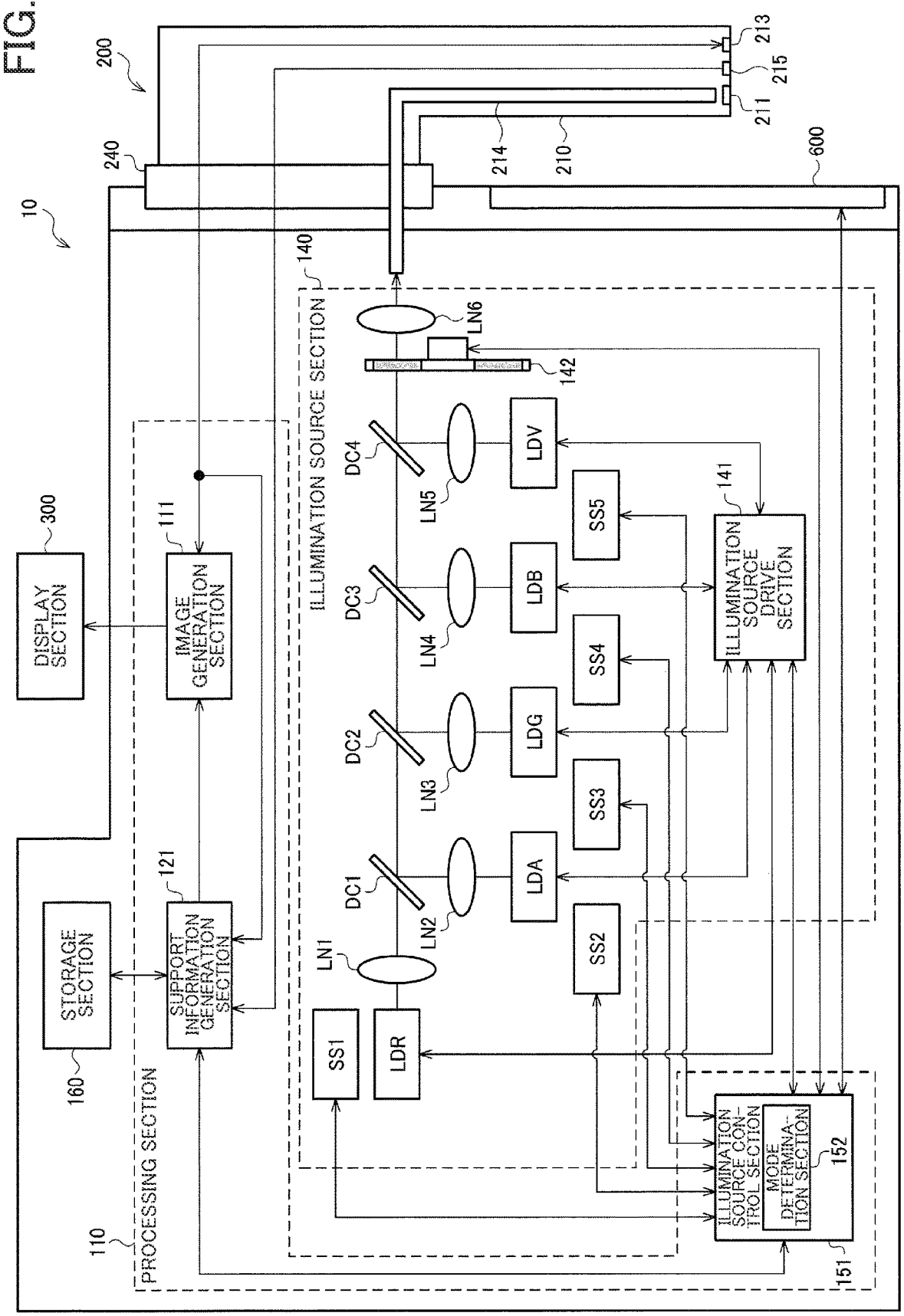
FIG. 1 is a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

This specification is directed to an endoscope for digestive organs, however, an applicable target of a method disclosed in this specification is not limited to this. That is, an endoscope apparatus described in this specification means general equipment including an insertion section for observing insides of recessed portions of various observation targets. For example, the endoscope apparatus includes a surgical endoscope used for surgery on abdominal cavities, joints, or the like.

1. Endoscope Apparatus

FIG. 1 is a configuration example of an endoscope apparatus 10 according to the present embodiment. The endoscope apparatus 10 includes a control device 100, a scope section 200, a display section 300, and an operation section 600. The control device 100 is also referred to as a main body section. The scope section 200 is also referred to as a scope, an imaging section, or an imaging device. The display section 300 is also referred to as a display, or a display device. The operation section 600 is also referred to as an operation panel, or an operation device.

First of all, a configuration of the endoscope apparatus 10 is described. Then, a method for optimizing illumination light in accordance with observation purposes is described.

The scope section 200 includes an insertion section 210 and a connector 240. The insertion section 210 has flexibility and can be inserted into a body cavity of a living body. The body cavity of the living body is an object in the present embodiment. The connector 240 is disposed at an end of the scope section 200 to make the scope section 200 attachable to/detachable from the control device 100.

The insertion section 210 includes an illumination lens 211, an imaging section 213, and a distance measurement sensor 215 at a distal end. The illumination lens 211 outputs illumination light toward the object. The imaging section 213 captures an image by receiving the illumination light reflected or scattered from a surface of the object. The distance measurement sensor 215 measures a distance from the distal end of the insertion section 210 to the object. The insertion section 210 also includes a light guide 214 that guides the illumination light emitted from an illumination source section 140 to the illumination lens 211.

The illumination lens 211 spreads the illumination light guided by the light guide 214 at a desired radiation angle. FIG. 1 illustrates one illumination lens disposed at the distal end of the insertion section 210, however, a plurality of illumination lenses may be disposed at the distal end of the insertion section 210. The light guide 214 is an optical fiber bundle, for example. The imaging section 213 includes an imaging optical system and an image sensor. The image sensor is a CMOS imager of a primary color type or a complementary color type, for example. The distance measurement sensor 215 is a distance measurement sensor adopting a time of flight (TOF) method, or an ultrasonic distance measurement sensor, for example. Instead of using the distance measurement sensor, the distance may be measured by using an imaging section 213 adopting a stereoscopic optical system. In order to use the distance measurement sensor adopting the TOF method, light having a long wavelength such as infrared light may be used.

The insertion section 210 may include various functions or mechanisms not illustrated. For example, the insertion section 210 may include a scope operation section for operating the scope section 200, a curving mechanism for curving a distal end portion, a forceps hole for inserting forceps or the like, a treatment tool such as an electrosurgical knife used for treatment, an air and water supply pipe for spouting or sucking liquid or gas, or the like. Alternatively, some of component elements included in the insertion section 210 may be omitted. For example, the distance measurement sensor 215 may be omitted in an embodiment that does not use a distance measurement function.

The control device 100 controls sections of the endoscope apparatus 10, and performs image processing on an image captured by the scope section 200. The control device 100 includes the illumination source section 140, a processing section 110, and a storage section 160.

The illumination source section 140 generates the illumination light and inputs the generated illumination light into the light guide 214. The illumination source section 140 can generate the illumination light having various spectral characteristics. Specifically, the illumination source section 140 includes an illumination source LDR that emits red light, an illumination source LDA that emits amber light, an illumination source LDG that emits green light, an illumination source LDB that emits blue light, an illumination source LDV that emits violet light, lenses LN1 to LN6, dichroic mirrors DC1 to DC4, light sensors SS1 to SS5, an illumination source drive section 141, and a filter section 142. The configuration of the illumination source section 140 is not limited to the configuration illustrated in FIG. 1. For example, the light sensors may be omitted. Alternatively, a light multiplex section using an optical fiber may be disposed instead of the dichroic mirrors DC1 to DC4.

The illumination sources LDR, LDA, LDG, LDB, and LDV are light emitting diodes (LDEs), or semiconductor lasers, for example. The red light emitted from the illumination source LDR has a peak wavelength of 635 nm. The amber light emitted from the illumination source LDA has a peak wavelength of 600 nm. The green light emitted from the illumination source LDG has a peak wavelength of 532 nm. The blue light emitted from the illumination source LDB has a peak wavelength of 445 nm. The violet light emitted from the illumination source LDV has a peak wavelength of 405 nm. These types of light are narrow band light having a half-value width of several tens nm, for example. The light emitted from each illumination source is not limited to this. That is, the red light may have the peak wavelength in a wavelength region from 615 to 680 nm, the amber light from 586 to 615 nm, the green light from 495 to 585 nm, the blue light from 440 to 495 nm, and the violet light from 400 to 440 nm. Each light may be broad light.

The lens LN1 inputs the light emitted by the illumination source LDR into the dichroic mirror DCL. Similarly, the lenses LN2, LN3, LN4, and LN5 respectively input the light emitted by the illumination sources LDA, LDG, LDB, and LDV into the dichroic mirrors DC1, DC2, DC3, and DC4.

The dichroic mirror DC1 allows the light emitted by the illumination source LDR to pass through and reflects the light emitted by the illumination source LDA. Similarly, the dichroic mirrors DC2, DC3, and DC4 respectively allow the light from the dichroic mirrors DC1, DC2, and DC3 to pass through and reflect the light emitted by the illumination sources LDG, LDB, and LDV.

The filter section 142 has a switchable configuration between a filter and a passage part. A plurality of filters may be disposed. The passage part allows the light from the dichroic mirror DC4 to pass through without changing the spectral characteristic. The filter has a spectral transmittance characteristic, and allows the light in a wavelength region corresponding to the spectral transmittance characteristic to pass through out of the light from the dichroic mirror DC4. The illumination sources LDR, LDA, LDG, LDB, and LDV are configured such that any one or more of the illumination sources can emit light. When at least one of the five illumination sources is selected to emit light, and the filter is selected in the filter section 142, the illumination light having a desired spectral characteristic can be implemented.

The lens LN6 inputs the light that has passed through the filter section 142 into the light guide 214.

The illumination source drive section 141 is controlled by an illumination source control section 151 so as to drive the illumination sources LDR, LDA, LDG, LDB, and LDV. The illumination source control section 151 will be described later. For example, when the illumination sources LDR, LDA, LDG, LDB, and LDV are the LEDs or the semiconductor lasers, the illumination source drive section 141 outputs a driving current to each illumination source to cause the illumination source to emit light.

The light sensors SS1, SS2, SS3, SS4, and SS5 are disposed at positions where the light sensors can detect leaking light from the illumination sources LDR, LDA, LDG, LDB, and LDV, respectively. The leaking light means light emitted outside optical paths entering the lenses L1 to L5.

The processing section 110 includes an image generation section 111, a support information generation section 121, and the illumination source control section 151. There may be various types of hardware that implement the processing section 110. For example, the image generation section 111, the support information generation section 121, and the illumination source control section 151 may be integrally implemented as a processor or an application specific integrated circuit (ASIC). Alternatively, each section may be independently implemented as a processor or an ASIC. Alternatively, two of the component elements such as the image generation section 111 and the support information generation section 121 may be integrally implemented as a processor or an ASIC. The processing section 210 is also referred to as a controller, and the control device 100 is also referred to as a processing device.

The image generation section 111 generates a display image based on an image signal from the imaging section 213. Specifically, the illumination source section 140 emits display illumination light for capturing a display image and support illumination light for generating support information in a time-division manner. The image generation section 111 generates the display image from the image signal acquired when the display illumination light is irradiated to the object. The image generation section 111 performs image processing including a process for generating an RGB image by an interpolation process of the image signal, a white balance process, or a grayscale transmission process, for example. The image generation section 111 also superimposes display content based on the support information generated by the support information generation section 121 on the display image, and outputs the display image to the display section 300.

The display section 30) is a display device such as a liquid crystal display, for example. The display section 300 displays the display image output by the image generation section 111. As a result, the image captured using the display illumination light and the support information superimposed on the image are presented to a user of the endoscope apparatus 10.

The support information generation section 121 generates the support information from the image signal acquired when the support illumination light is irradiated to the object. The support information is information for supporting diagnosis or treatment performed by a physician or a surgeon using the endoscope apparatus 10. The support information generation section 121 performs an inference process by means of artificial intelligence (AI). That is, the support information generation section 121 extracts the support information from the input image signal through the inference process. As for the AI, any of various image recognition methods or machine learning methods may be adopted. Machine learning is a process of making various inferences based on learning results. A representative example of the AI is a neural network. However, the AI is not limited to this, and various known machine learning methods may be used as the AI in the present embodiment.

The storage section 160 is a semiconductor memory, or a storage device such as a hard disk drive, for example. The storage section 160 stores information on a trained model. The support information generation section 121 performs the inference process by the AI based on the trained model. There may be various types of hardware adoptable as the support information generation section 121 that performs the inference process. For example, the support information generation section 121 is a general purpose processor such as a CPU. In this case, the storage section 160 stores a program including an inference algorithm and a parameter used for the inference algorithm as information on the trained model. Alternatively, the support information generation section 121 may be a single purpose processor implementing the inference algorithm as hardware. In this case, the storage section 160 stores the parameter used for the inference algorithm as the information on the trained model.

The inference algorithm is the neural network. The neural network includes an input layer that accepts input data, an intermediate layer that performs a calculation process to the data input through the input layer, and an output layer that outputs data based on a calculation result output from the intermediate layer. Nodes included in the input layer are connected to nodes included in the intermediate layer, and the nodes included in the intermediate layer are connected to nodes included in the output layer. A weight coefficient of the connection between the nodes corresponds to the parameter described above.

The illumination source control section 151 controls the spectral characteristic of the illumination light. That is, the illumination source control section 151 outputs a control signal to the illumination source drive section 141 to cause each illumination source to emit light or turn off, or to control a light emission amount of each illumination source. The illumination source control section 151 also controls the filter section 142 to control the spectral characteristic of the illumination light. The illumination source control section 151 also controls a light emission timing of each illumination source in accordance with a predetermined light emission sequence. The illumination source control section 151 also performs a feedback control based on output signals from the light sensors SS1 to SS5 such that the light emission amounts of the illumination sources LDR, LDA, LDG, LDB, and LDV become desired values.

The illumination source control section 151 causes the illumination source section 140 to emit the display illumination light and the support illumination light in a time-division manner based on the control described above. The endoscope apparatus 10 has a presence diagnosis mode, a qualitative diagnosis mode, and a treatment support mode. Each mode will be described later in detail. In each of the presence diagnosis mode, qualitative diagnosis mode, and treatment support mode, the support illumination light has a different spectral characteristic. That is, the illumination source control section 151 controls the illumination source section 140 to emit the support illumination light having the spectral characteristic corresponding to the set mode. The illumination source control section 151 includes a mode determination section 152 that switches a determination mode based on the support information generated by the support information generation section 121. The mode determination section 152 is included in the illumination source control section 151 in FIG. 1, however, the mode determination section 152 may be disposed outside the illumination source control section 151. Alternatively, the determination mode may be switched based on information input from the operation section 600. The operation section 600 is a device used by a user such as a physician or a surgeon for operating the endoscope apparatus 10. For example, the operation section 600 includes a button, a dial, a foot switch, or a touch panel.

The determination mode is a mode corresponding to a determination criterion used when the support information generation section 121 generates the support information. That is, the support information generation section 121 in a first determination mode generates the support information based on a first determination criterion, and the support information generation section 121 in a second determination mode different from the first determination mode generates the support information based on a second determination criterion different from the first determination criterion. The determination criterion in each determination mode only needs to suit an observation purpose of the determination mode. That is, although the support information required to be presented differs depending on the observation purpose, it is only necessary to adopt the determination criterion allowing extraction of the support information suitable for the observation purpose from image information. For example, the processing section 110 may infer the determination mode based on the image information, and set the inferred determination mode. Setting the determination mode sets the determination criterion for generating the support information. An example described hereinafter is a case where the first determination mode is the presence diagnosis mode and the second determination mode is the qualitative diagnosis mode. The presence diagnosis mode and the qualitative diagnosis are examples of the determination mode set in accordance with the observation mode used by the physician or surgeon in the endoscopic observation, however, the determination mode may be another predetermined mode. Furthermore, in the following description, a trained model corresponding to each determination mode is used. However, the configuration is not limited to this, and it is only necessary that the determination criterion differs for each determination mode.

The support information is generated by the trained model corresponding to each determination mode. That is, the storage section 160 stores information on the trained model corresponding to the presence diagnosis mode, information on the trained model corresponding to the qualitative diagnosis mode, and information on the trained model corresponding to the treatment support mode. The support information generation section 121 generates the support information from the image signal through the inference process based on the trained model corresponding to the set determination mode. The trained model for each determination mode has learned as follows, for example. A learning method is described below with an example in the presence diagnosis mode, however, the same applies to the qualitative diagnosis mode and the treatment support mode.

Training data includes an image captured using the support illumination light in the presence diagnosis mode and annotation information added to the image by an expert such as a physician or a surgeon. The annotation information is information desired to be displayed as the support information, and includes information on a position or contour of a lesion part in the presence diagnosis mode, for example. A plurality of sets of the image and annotation information are prepared as the training data. The image in the training data is input to the inference algorithm, and the support information is inferred from the image by the inference algorithm. Then, feedback is performed on the parameter of the inference algorithm such that the support information becomes similar to the annotation information. The feedback is repeated using the plurality of sets of the image and annotation information so as to perform learning.

There may be various environments in which a learning process is performed. For example, the processing section 110 of the endoscope apparatus 10 may perform the learning process, and the storage section 160 may store information on the trained model generated by the learning process. Alternatively, an information processing device such as a personal computer (PC) may perform the learning process, and the storage section 160 of the endoscope apparatus 10 may store the information on the trained model generated by the learning process.

The "lesion" used in this specification means a portion that the support information generation section 121 detects as having a possibility of being a lesion, and it is the physician or surgeon that determines whether the portion is an actual lesion. That is, the "lesion" detected by the support information generation section 121 is a lesion candidate. The lesion candidate is also referred to simply as a lesion or a lesion part in this specification.

2. First Embodiment

Hereinafter described is a method for optimizing the illumination light in accordance with the observation purposes. In a first embodiment, the mode is automatically switched from the presence diagnosis mode to the qualitative diagnosis mode based on the support information. As described above, the display illumination light and the support illumination light are emitted in a time-division manner, and the support illumination light is set to have an optimum spectral characteristic in each mode of the presence diagnosis mode and the qualitative diagnosis mode.

First of all, a light emission sequence and an imaging sequence in each mode are described. Content of the support information and a display method of the support information are also described.

Figure 2:
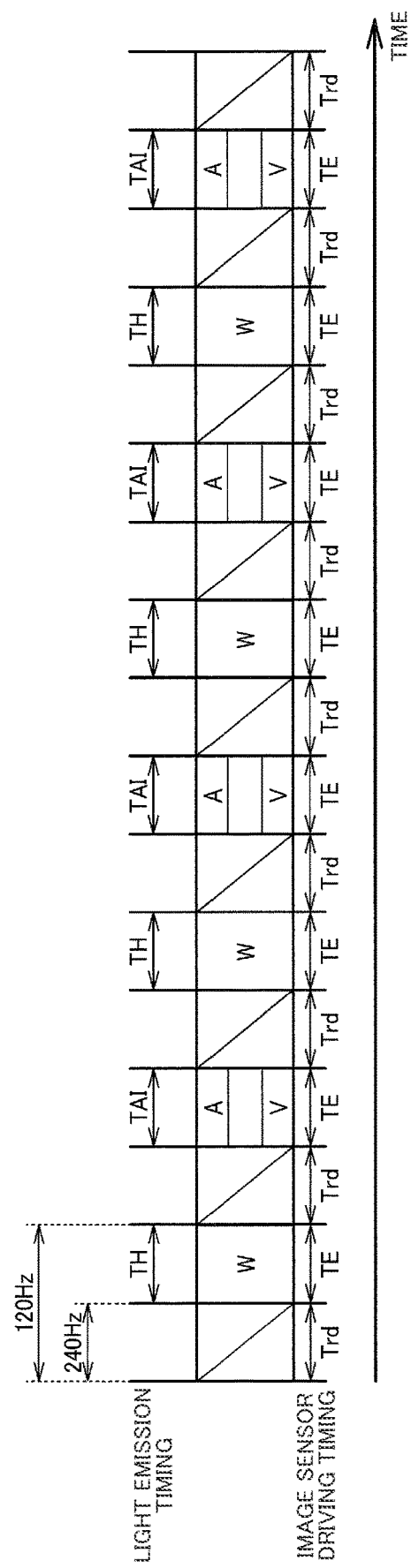
FIG. 2 is a diagram illustrating a light emission sequence and an imaging sequence in a presence diagnosis mode.

FIG. 2 is a diagram illustrating the light emission sequence and the imaging sequence in the presence diagnosis mode. In a driving sequence of the image sensor, a readout period Trd when the image signal is read out and an exposure period TE when an image of the object is captured are repeated. When the display image is displayed at a frame rate of 60 Hz, a repetition rate of the period Trd and the period TE is 120 Hz.

The illumination source control section 151 causes the illumination source section 140 to emit the illumination light in periods TH and TAI each corresponding to the exposure period TE. The illumination source control section 151 causes the illumination source section 140 to emit white light W as the display illumination light in the period TH. The white light is the display illumination light. The illumination source control section 151 causes the illumination source section 140 to emit amber light A and violet light V as the support illumination light in the period TAI. The illumination source control section 151 causes the illumination source section 140 to alternately emit the white light, and the amber light A and violet light V.

The violet light is suitable for acquiring characteristics of a blood vessel in a surface layer of mucosa or a glandular duct structure. The amber light is suitable for acquiring characteristics of a blood vessel in a deep part of mucosa, redness, or inflammation. That is, the support information generation section 121 detects the lesion detectable based on the characteristics of the blood vessel in the surface layer of the mucosa or the glandular duct structure, or the lesion detectable based on the characteristics of the blood vessel in the deep part of the mucosa, the redness, or the inflammation, as the support information. In the presence diagnosis mode, using the violet light and the amber light allows detection of presence of the lesion in a wide range such as cancer and inflammatory diseases.

Figure 3:
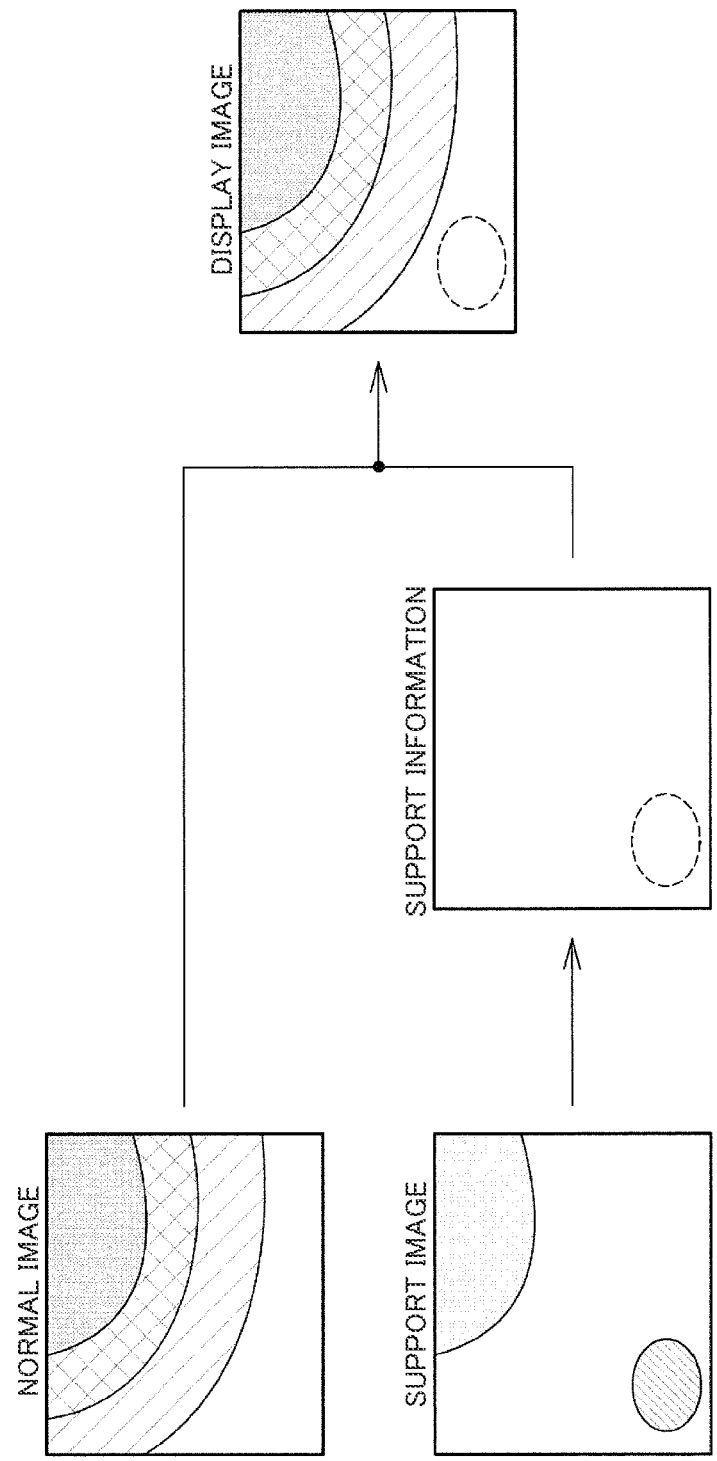
FIG. 3 is a diagram illustrating a generation process of a display image.

FIG. 3 is a diagram illustrating a generation process of the display image. The image generation section 111 generates a normal image from the image signal acquired in the period TH in FIG. 2. The normal image is a white light image.

The image generation section 111 also generates a support image from the image signal acquired in the period TAI in FIG. 2. The support image is an image of the object irradiated with the amber light and the violet light. The support information generation section 121 generates the support information from the support image. In FIG. 3, a hatched part at the lower left of the support image is the lesion, and a contour of the lesion is detected as the support information. The contour of the lesion is shown by a broken line in FIG. 3. The image generation section 111 may omit generating the support image, and the image signal acquired in the period TAI may be directly input to the support information generation section 121.

The image generation section 111 uses the normal image as the display image, and further superimposes a display of the contour of the lesion on the display image. The display image including the support information is displayed on the display section 300. The physician or surgeon using the endoscope apparatus 10 can recognize the position or contour of the lesion candidate from the display image. The physician or surgeon has learned how the lesion looks in the normal image by experience or learning. Thus, using the normal image as the display image and adding the support information thereon can facilitate observation and diagnosis of the lesion by the physician or surgeon.

Next, the light emission sequence in the qualitative diagnosis mode is described. The qualitative diagnosis mode may include a plurality of diagnosis modes. In the first embodiment, the qualitative diagnosis mode includes a narrow band imaging (NBI) mode and a simulative coloring mode.

Figure 4:
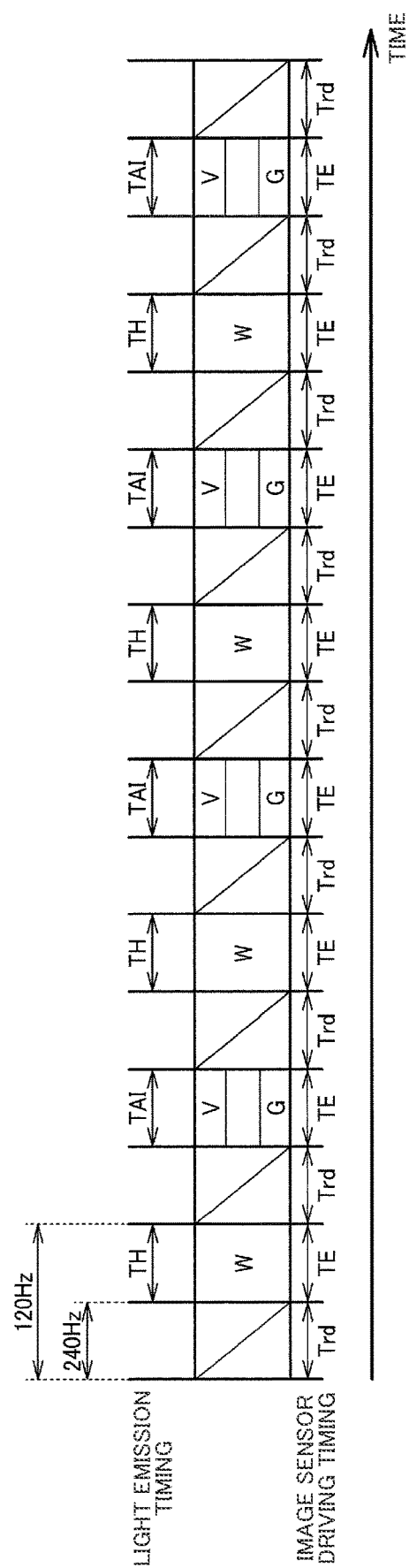
FIG. 4 is a diagram illustrating a light emission sequence and an imaging sequence in an NBI mode.

FIG. 4 is a diagram illustrating the light emission sequence and the imaging sequence in the NBI mode. Description that is common to that of FIG. 2 is omitted.

In the NBI mode, the illumination source control section 151 causes the illumination source section 140 to emit the violet light V and the green light G in the period TAI. A combination of the violet light V and the green light G is used for NBI. However, a light amount ratio between the violet light V and the green light G only needs to suit the inference process by the AI, and does not have to be a light amount ratio in normal NBI.

The support information in the qualitative diagnosis mode such as the NBI mode is qualitative support information about the lesion detected in the presence diagnosis mode. The qualitative support information may include various types of information used for diagnosis of the lesion, such as progress of the lesion, an extent of a symptom, a range of the lesion, or a boundary between the lesion and a normal part. The support information may be a classification result based on a trained model that has learned classification in accordance with a classification criterion defined by a learned society or the like, for example.

In the NBI mode, the support information generation section 121 generates the qualitative support information by processing based on the trained model corresponding to the NBI mode. The qualitative support information in the NBI mode is the classification result classified in accordance with various NBI classification criteria. The NBI classification criteria include VS classification that is a gastric lesion classification criterion, and JNET classification. NICE classification, or EC classification that are colorectal lesion classification criteria, for example.

Figure 5:
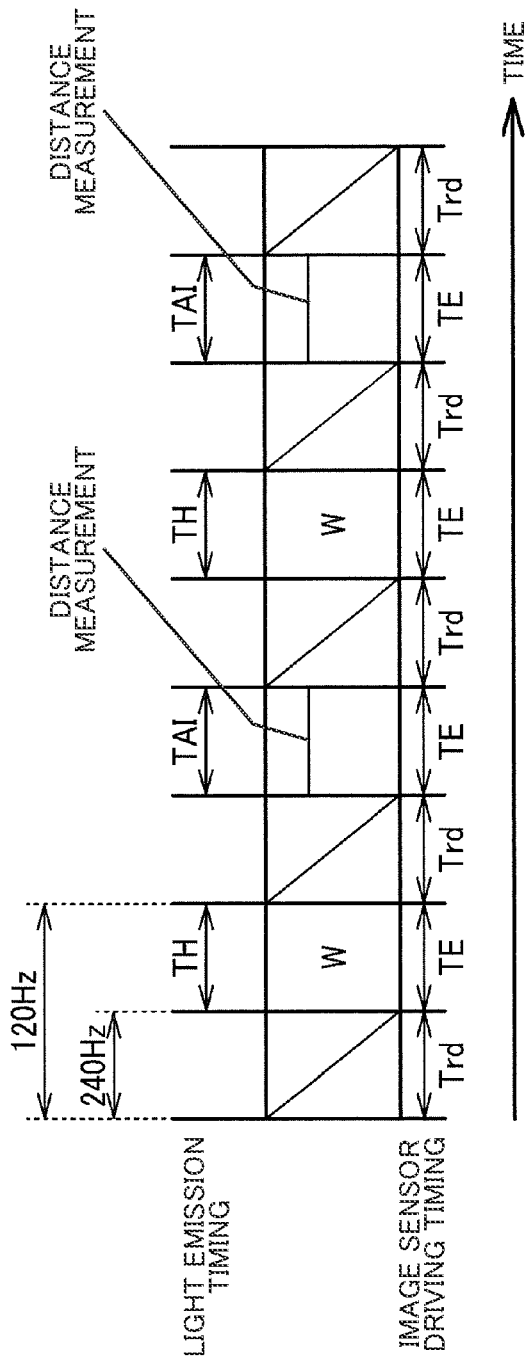
FIG. 5 is a diagram illustrating a light emission sequence and an imaging sequence in a simulative coloring mode.

FIG. 5 is a diagram illustrating the light emission sequence and the imaging sequence in the simulative coloring mode. Description that is common to that of FIG. 2 or the like is omitted.

In the simulative coloring mode, the processing section 110 measures a distance to the object with the distance measurement sensor 215 in the period TAI. Specifically, the processing section 110 acquires information on irregularities of an object surface by the distance measurement. The information on the irregularities is a depth map, for example. The support information generation section 121 generates the support information based on a result of the distance measurement. The support information is information on simulative coloring such as information on light and shade of coloring in each pixel. When the object is colored with a splayed agent, a recessed portion in the object surface is deeply colored. The support information generation section 121 generates the support information on the simulative coloring that reproduces the coloring with the sprayed agent.

The image generation section 111 performs a coloring process based on the support information on the normal image captured using the display illumination light so as to generate the display image. That is, the image generation section 111 adds color to each pixel in accordance with the light and shade of each pixel indicated by the support information. For example, in a case of the simulative coloring of indigo carmine, the simulative coloring is performed using blue imitating the indigo carmine.

The support information generation section 121 generates the qualitative support information from the display image applied with the coloring process based on the support information. The trained model corresponding to the simulative coloring mode has learned with training data including images applied with the coloring process and annotation information added to the images by the expert such as the physician or surgeon. The support information generation section 121 uses the trained model to generate the support information from the simulatively colored image. In order to add the annotation, various classification criteria using coloring with splayed pigment can be used. The support information generated by the support information generation section 121 is a classification result in accordance with a classification criterion used for learning.

Figure 6:
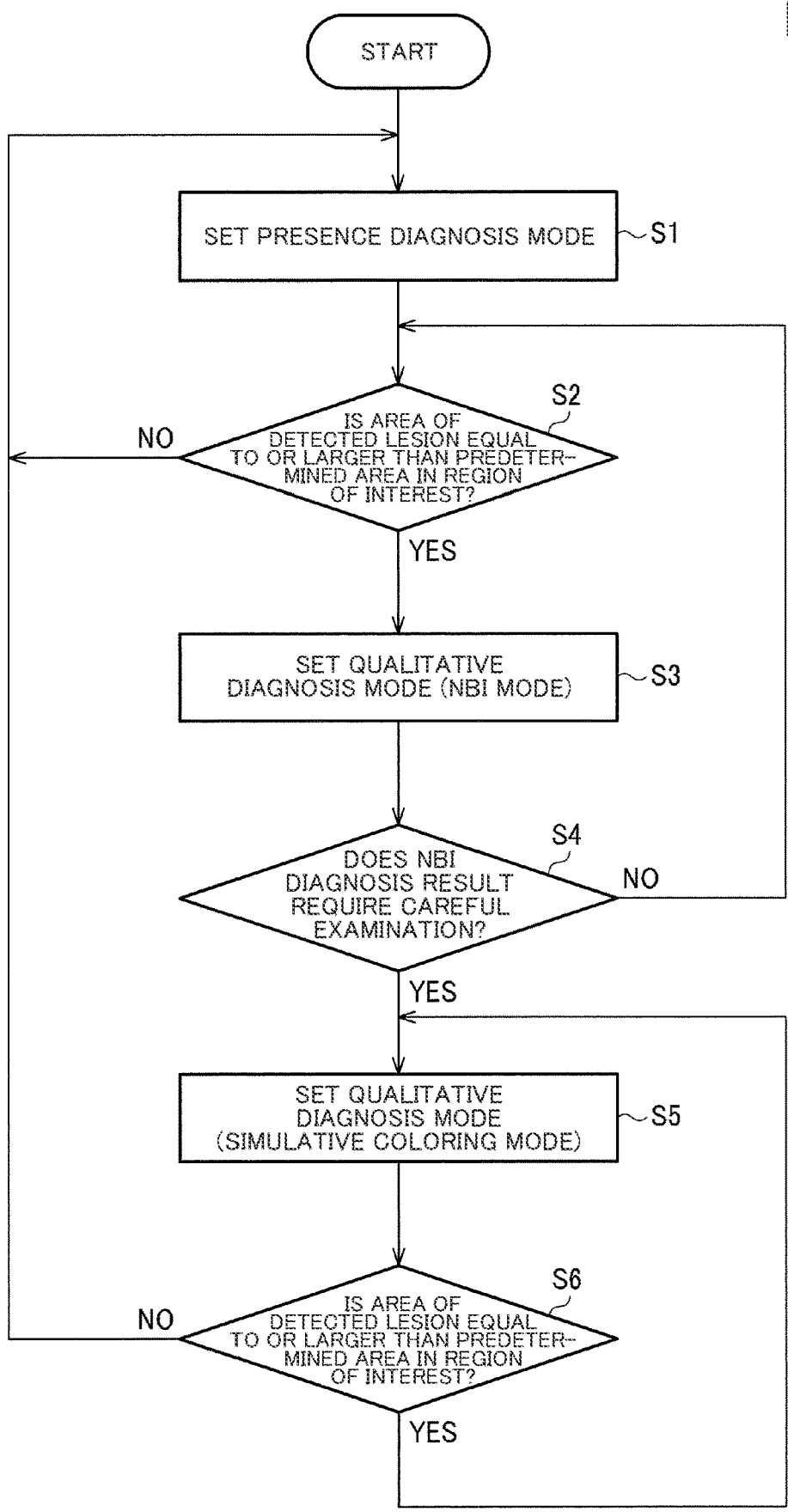
FIG. 6 is a flowchart illustrating procedures of a process performed by a processing section for switching a mode from the presence diagnosis mode to a qualitative diagnosis mode.

Next, a method for automatically switching the mode from the presence diagnosis mode to the qualitative diagnosis mode based on the support information is described. FIG. 6 is a flowchart illustrating procedures of a process performed by the processing section 110 for switching the mode from the presence diagnosis mode to the qualitative diagnosis mode.

The mode determination section 152 sets the mode to the presence diagnosis mode at a step S1. The illumination source control section 151 causes the illumination source section 140 to emit the white light, and the amber light A and violet light V in a time-division manner. The support information generation section 121 generates the support information by processing based on the trained model corresponding to the presence diagnosis mode.

Next, the mode determination section 152 determines whether an area of the lesion indicated by the support information is equal to or larger than a predetermined area in a region of interest in a step S2. When the lesion is equal to or larger than the predetermined area, the mode determination section 152 sets the mode to the NBI mode in the qualitative diagnosis mode in a step S3. When the lesion is not equal to or larger than the predetermined area, the process returns to the step S1.

Figure 7:
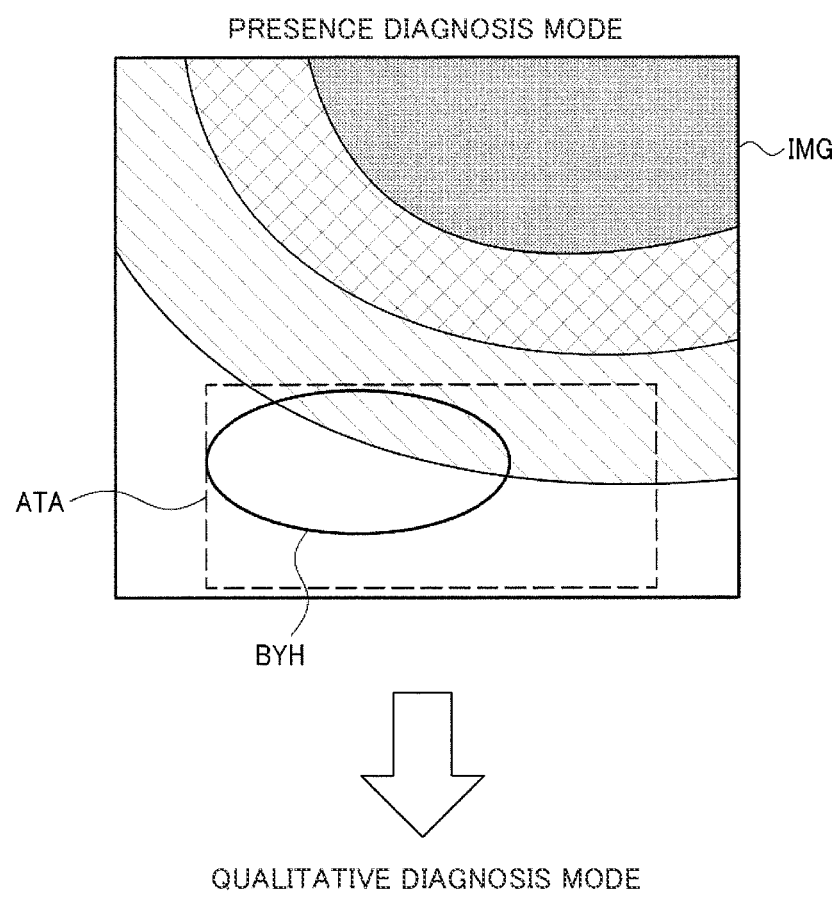
FIG. 7 is a diagram illustrating a method for determining whether to switch the mode from the presence diagnosis mode to the qualitative diagnosis mode.

FIG. 7 is a diagram illustrating a method for determining whether to switch the mode from the presence diagnosis mode to the qualitative diagnosis mode. IMG represents an image captured in the presence diagnosis mode, and a hatched part in the image schematically shows an object in a luminal form. The upper right of the image IMG is an inner depth of a lumen, and a distance between a wall surface and the imaging section becomes shorter toward the lower left. Assume that the support information generation section 121 detects a lesion BYH at a lower part of the image IMG, i.e., on the wall surface of the lumen. An ellipse drawn by a solid line represents the support information generated by the support information generation section 121, and is the contour of the lesion BYH in this case.

ATA represents the region of interest. For example, the region of interest may be set by the physician or surgeon operating the endoscope apparatus 10 by means of the operation section 600. The region of interest ATA may be set at an arbitrary position with an arbitrary area in the image IMG. The region of interest ATA is set in a lower region of the image IMG in FIG. 7. The mode determination section 152 obtains an area of the lesion BYH in the region of interest ATA, and determines whether the area is equal to or larger than a predetermined value. For example, the mode determination section 152 counts a number of pixels in an overlapping region of the region of interest ATA and the lesion BYH. The mode determination section 152 determines whether the number of pixels is equal to or larger than the predetermined value. Alternatively, the mode determination section 152 obtains a ratio between the counted number of pixels and a number of pixels in the region of interest ATA, and determines whether the ratio is equal to or higher than a predetermined value. When the mode determination section 152 determines that the area of the lesion BYH is equal to or larger than the predetermined value, the mode determination section 152 switches the mode from the presence diagnosis mode to the NBI mode in the qualitative diagnosis mode. The predetermined value for area determination may be set by the physician or surgeon operating the endoscope apparatus 10 by means of the operation section 600, for example.

In the NBI mode in the step S3, the illumination source control section 151 causes the illumination source section 140 to emit the white light W, and the violet light V and green light G in a time-division manner. The support information generation section 121 generates the support information by the processing based on the trained model corresponding to the NBI mode. The support information generation section 121 generates the qualitative support information about the lesion detected in the presence diagnosis mode.

Next, the mode determination section 152 determines whether a careful examination is further required based on the qualitative support information generated by the support information generation section 121 in a step S4. When the mode determination section 152 determines that the careful examination is not required, the process returns to the step S2. When the mode determination section 152 determines that the careful examination is required, the mode determination section 152 sets the mode to the simulative coloring mode in the qualitative diagnosis mode in a step S5.

In the simulative coloring mode, illumination by the white light W and distance measurement are performed in a time-division manner. The support information generation section 121 generates the support information by the processing based on the trained model corresponding to the simulative coloring mode. The image generation section 111 performs the coloring process on the display image based on the support information. The support information generation section 121 generates the qualitative support information from the display image applied with the coloring process based on the support information. That is, the classification result of the lesion in accordance with the classification criterion using the coloring is generated as the support information.

Next, the mode determination section 152 determines whether an area of the lesion detected in the step 5 is equal to or larger than a predetermined area in the region of interest in a step S6. A determination method is the same as that in the step S2. When the lesion is equal to or larger than the predetermined area, the process returns to the step S5. When the lesion is not equal to or larger than the predetermined area, the process returns to the step S1.

Figure 8:
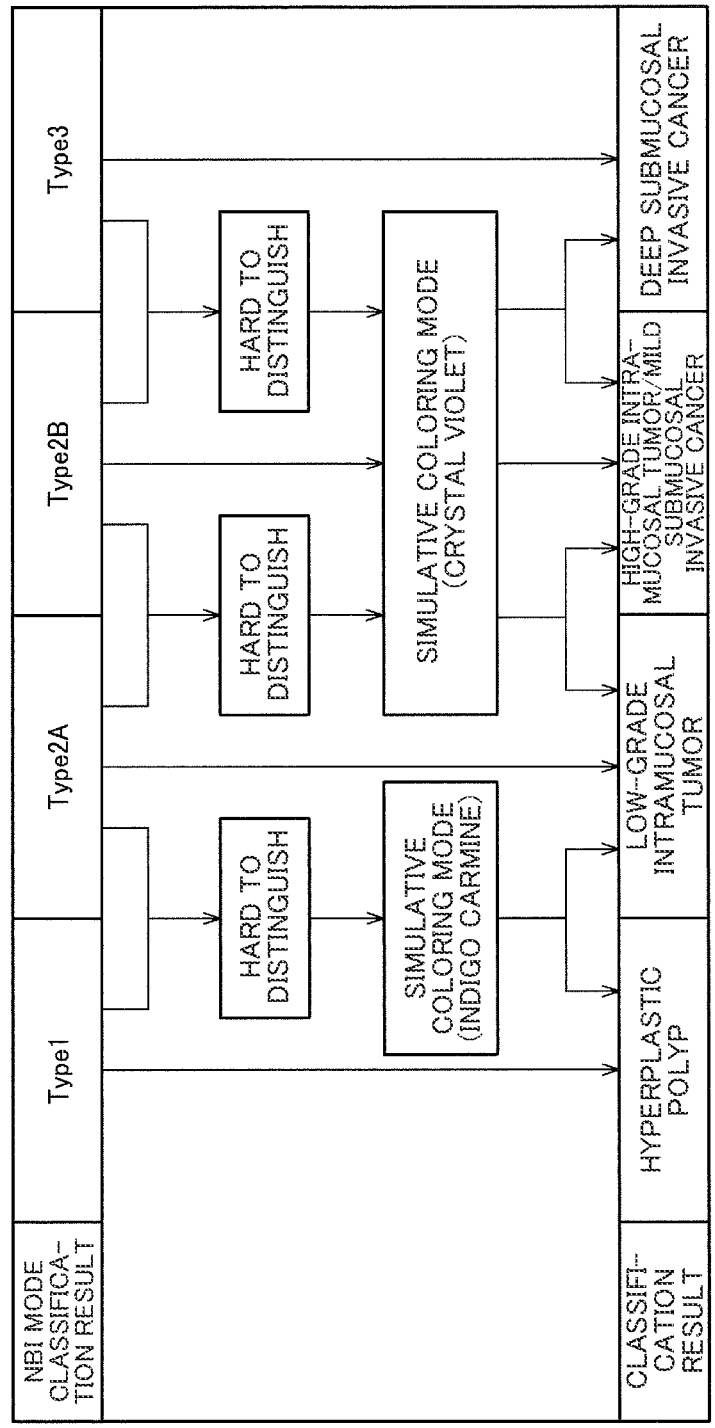
FIG. 8 is an example of automatic classification in the qualitative diagnosis mode.

FIG. 8 is an example of automatic classification in the qualitative diagnosis mode. FIG. 8 illustrates a flow of the automatic classification using the JNET classification criterion. This flow is performed in the steps S3 to S5 in FIG. 6.

In a learning stage, the physician or surgeon tags a classification result to an image based on the JNET classification. That is, the physician or the like circles the lesion part in the image with a pointing device or the like, for example, so that the position or contour of the lesion is tagged with the classification of the lesion. Then, the trained model is generated using the tag information and the images as the training data. When the diagnosis is made using the endoscope apparatus, the inference process is performed based on this trained model to implement the automatic classification described below. That is, the inference process generates the position or contour of the lesion and the classification of the lesion as the support information.

As illustrated in FIG. 8, in the NBI mode, the support information generation section 121 classifies the lesion detected in the presence diagnosis mode as Type 1, Type 2A, Type 2B, or Type 3. These Types are classifications characterized by a blood vessel pattern of the mucosa and a surface structure of the mucosa. The support information generation section 121 outputs a probability that the lesion belongs to Type 1, a probability that the lesion belongs to Type 2A, a probability that the lesion belongs to Type 2B, and a probability that the lesion belongs to Type 3. In addition to a final classification result, classification results at this stage may be displayed on the display image by characters or the like.

The support information generation section 121 determines whether distinction of the lesion is difficult based on the classification result in the NBI mode.

That is, when the probabilities of belonging to Type 1 and Type 2A are close, the support information generation section 121 determines that the distinction is difficult. In this case, the mode determination section 152 sets the mode to the simulative coloring mode for simulatively reproducing the indigo carmine coloring. In the simulative coloring mode, the support information generation section 121 classifies the lesion as a hyperplastic polyp or a low-grade intramucosal tumor based on the simulatively colored image. These classifications are characterized by pit patterns in the colored images by the indigo carmine. On the other hand, when the probability of belonging to Type 1 is equal to or higher than a threshold value, the support information generation section 121 classifies the lesion as the hyperplastic polyp, and the mode determination section 152 does not switch the mode to the simulative coloring mode. Furthermore, when the probability of belonging to Type 2A is equal to or higher than a threshold value, the support information generation section 121 classifies the lesion as the hyperplastic polyp, and the mode determination section 152 does not switch the mode to the simulative coloring mode.

When the probabilities of belonging to Type 2A and Type 2B are close, the support information generation section 121 determines that the distinction is difficult. In this case, the mode determination section 152 sets the mode to the simulative coloring mode for simulatively reproducing crystal violet coloring. In the simulative coloring mode, the support information generation section 121 classifies the lesion as the low-grade intramucosal tumor, or a high-grade intramucosal tumor or mild submucosal invasive cancer based on the simulatively colored image. These classifications are characterized by pit patterns in the colored images by the crystal violet.

Although detailed description is hereafter omitted, when it is determined that the lesion belongs to Type 2B, the mode is set to the simulative coloring mode for simulatively reproducing the crystal violet coloring, and the lesion is classified as the high-grade intramucosal tumor or the mild submucosal invasive cancer. When distinction between Type 2B and Type 3 is difficult, the mode is set to the simulative coloring mode for simulatively reproducing the crystal violet coloring, and the lesion is classified as the high-grade intramucosal tumor or mild submucosal invasive cancer, or deep submucosal invasive cancer. When it is determined that the lesion belongs to Type 2B, the mode is not switched to the simulative coloring mode, and the lesion is classified as the deep submucosal invasive cancer.

The image generation section 111 adds the classification result described above and the detected position or contour of the lesion to the display image as the support information to display the display image on the display section 300.

Figure 9:
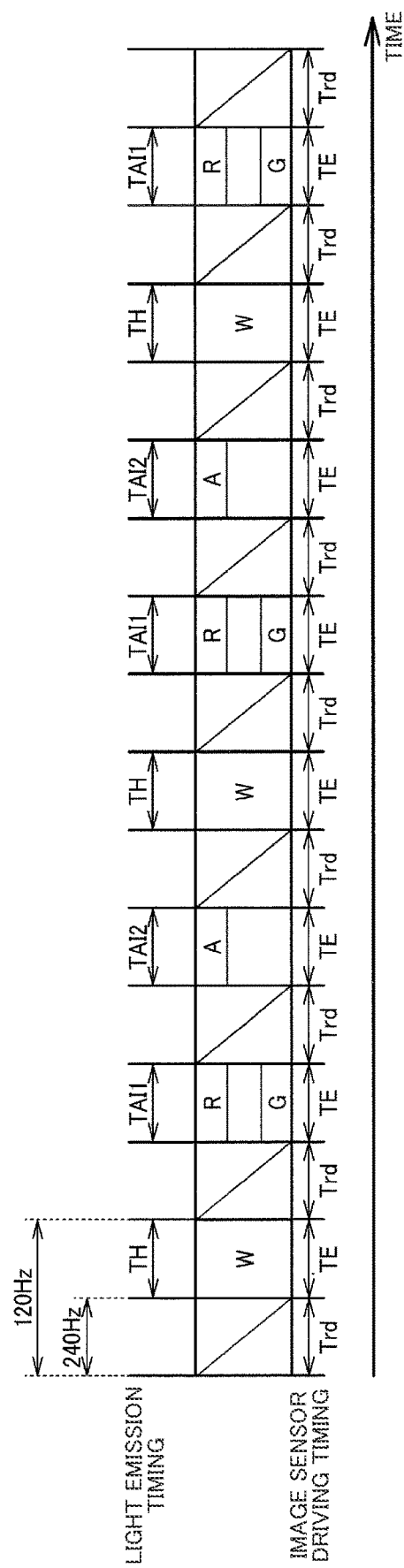
FIG. 9 is a diagram illustrating a light emission sequence and an imaging sequence in a UC inflammation diagnosis mode.

The spectral characteristic of the support illumination light is changed according to the mode in the first embodiment, however, the configuration is not limited to this, and a light amount, a light distribution characteristic, or an emission timing of the support illumination light may be changed according to the mode. For example, the light amount may be set in a diagnosis support mode so as to detect the lesion part detected in the presence diagnosis mode with appropriate brightness. Alternatively, the light distribution characteristic may be set in the diagnosis support mode so as to appropriately illuminate the lesion part detected in the presence diagnosis mode. For example, the light distribution can be changed by disposing a plurality of illumination lenses at the distal end of the scope section 200 and controlling the light amount output from each illumination lens. An example of changing the emission timing will be described later with reference to FIG. 9 in a second embodiment, for example. In FIG. 9, the support illumination light is emitted at two different timings in periods TAI1 and TAI2.

The endoscope apparatus 10 according to the embodiment described above includes the illumination source section 140, the imaging section 213, and the processing section 110. The illumination source section 140 can change an illumination property including at least one of the spectral characteristic, the light amount, the light distribution characteristic, and the emission timing of the illumination light to be emitted. The imaging section 213 captures the image of the object illuminated by the illumination light, and outputs the image signal. The processing section 110 sets the illumination property based on the support information for supporting the diagnosis or treatment. When the illumination property is a first illumination property, the processing section 110 changes the illumination property to a second illumination property based on first support information generated based on the image signal.

As a result, the illumination light can be optimized to have an optimum illumination property for the inference process by the AI. Accordingly, the support information can be inferred with high accuracy, and the highly accurate support information can be presented to the physician or surgeon. Specifically, the AI used here is supposed to output the support information necessary for the observation purpose. At this time, the optimum illumination light for the inference process by the AI can be emitted from the illumination source section 140. As a result, the support information suitable for the observation purpose can be inferred with high accuracy.

In the first embodiment, the first illumination property is the amber light A and the violet light V in the presence diagnosis mode, the second illumination property is the violet light V and the green light G in the NBI mode, the first support information is the position or contour of the lesion detected in the presence diagnosis mode, and the second support information is the classification result of the lesion in the NBI mode.

Furthermore, according to the present embodiment, the processing section 110 generates the support information based on the image signal. That is, the processing section 110 generates the first support information based on the image signal when the illumination property is the first illumination property, and generates the second support information including the diagnosis or treatment, content of which is different from that in the first support information, based on the image signal when the illumination property is the second illumination property.

Figure 15:
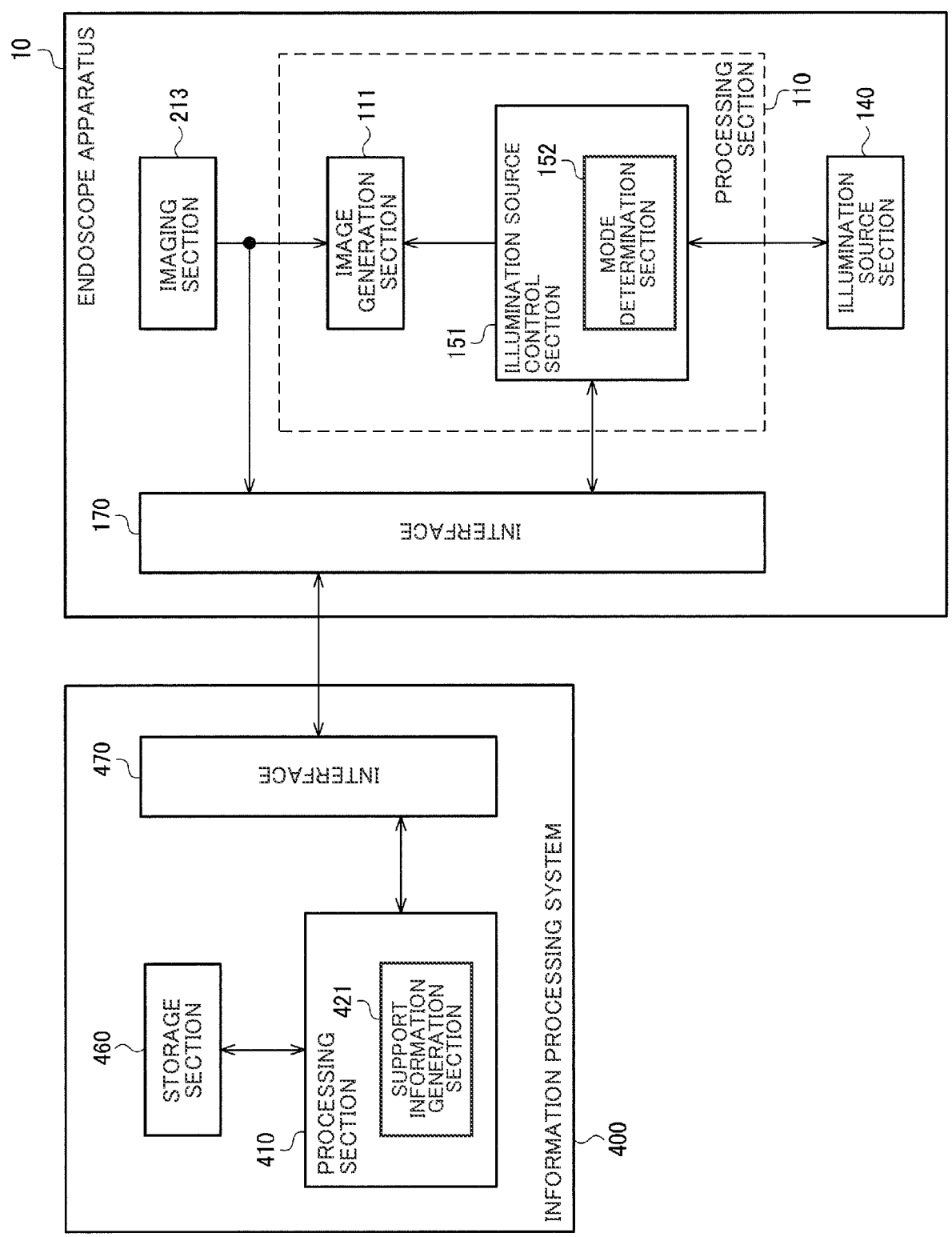
FIG. 15 is a configuration example of an endoscope system.

However, the support information generation section that generates the support information may be disposed outside the endoscope apparatus 10, as illustrated in FIG. 15. An endoscope apparatus system in FIG. 15 includes the endoscope apparatus 10 and an information processing system 400. In FIG. 15, the processing section 110 of the endoscope apparatus 10 does not include the support information generation section 121, but the endoscope apparatus 10 further includes an interface 170. The information processing system 400 includes an interface 470, a storage section 460, and a processing section 410. The processing section 410 includes a support information generation section 421.

The support information generation section 421 and the storage section 460 correspond to the support information generation section 121 and the storage section 160 in FIG. 1. That is, the image signal is input to the support information generation section 421 from the imaging section 213 via the interface 170 and the interface 470. The support information generation section 421 performs the inference process based on the trained model stored in the storage section 460 to generate the support information from the image signal. The support information is input to the mode determination section 152 via the interface 470 and the interface 170. The mode determination section 152 switches the determination mode based on the support information, and the information on the determination mode is input to the support information generation section 421 via the interface 170 and the interface 470.

The interfaces 170 and 470 may be any of various types of communication interface. For example, the interfaces 170 and 470 may be interfaces for establishing a network connection by LAN, WAN or the like. Alternatively, the interfaces 170 and 470 may be interfaces for cable communication such as a USB or the like, or interfaces for wireless communication such as proximity wireless communication or the like. The information processing system 400 may be an information processing device such as a PC or a server, for example. Alternatively, the information processing system 400 may be a cloud system where a plurality of information processing devices connected by a network perform information processing. In this case, functions of the processing section 410 are implemented by the information processing performed by the plurality of information processing devices included in the cloud system.

Furthermore, according to the present embodiment, when the determination mode in a generation process of the support information is the first determination mode, the processing section 110 sets the illumination property to the first illumination property and generates the first support information. The processing section 110 switches the determination mode to the second determination mode based on the first support information. The processing section 110 sets the illumination property to the second illumination property and generates the second support information in the second determination mode.

As a result, the mode can be automatically switched from the first determination mode to the second determination mode based on the first support information, and the illumination light having the illumination property corresponding to each determination mode can be emitted accordingly. Thus, the illumination light having the optimum illumination property for each determination mode can be emitted, and highly accurate or optimum support information can be generated in each determination mode to be presented to the physician or surgeon.

Furthermore, according to the present embodiment, the processing section 110 determines whether the first support information satisfies a predetermined condition. When the processing section 110 determines that the first support information satisfies the predetermined condition, the processing section 110 switches the mode from the first determination mode to the second determination mode.

As a result, the mode can be automatically switched from the first determination mode to the second determination mode when the first support information satisfies the predetermined condition in the first determination mode.

Furthermore, according to the present embodiment, the first determination mode is the presence diagnosis mode for diagnosing the presence of the lesion candidate included in the object. The first support information is information on the presence of the lesion candidate. The second determination mode is the qualitative diagnosis mode for diagnosing status of the lesion candidate. The second support information is information on the status of the lesion candidate.

As a result, the mode can be automatically switched from the presence diagnosis mode to the qualitative diagnosis mode based on the first support information in the presence diagnosis mode. Automatically switching the mode from the presence diagnosis mode to the qualitative diagnosis mode allows automatic presentation of the qualitative information about the lesion to the physician or surgeon in addition to the presence of the lesion. As a result, the qualitative support information useful for the physician or surgeon to diagnose the lesion can be automatically displayed on a monitor.

Furthermore, according to the present embodiment, the processing section 110 determines whether the first support information satisfies the predetermined condition that the area of the lesion candidate included in the first support information is equal to or larger than the predetermined value, or that an observation magnification of the imaging section is equal to or higher than a predetermined value. When the processing section 110 determines that the first support information satisfies the predetermined condition, the processing section 110 switches the mode from the first determination mode to the second determination mode.

When the physician or surgeon focuses on the lesion and brings the scope section 200 near the lesion, the area of the lesion candidate may become equal to or larger than the predetermined value. Alternatively, the physician or surgeon performs a magnifying observation for observing the lesion. Thus, when the area of the lesion candidate is equal to or larger than the predetermined value, or when the observation magnification of the imaging section is equal to or higher than the predetermined value, the mode is switched to the diagnosis support mode, so that the qualitative support information about the lesion focused on by the physician or surgeon can be presented to the physician or surgeon.

Furthermore, according to the present embodiment, the lesion candidate is a tumor candidate.

In the present embodiment, the tumor candidate is detected in the presence diagnosis mode, and when the tumor candidate satisfies the predetermined condition described above, the mode can be switched to the qualitative diagnosis mode. As a result, the qualitative support information about the tumor candidate such as a type of tumor can be presented to the physician or surgeon. The lesion is not limited to the tumor, and may be any abnormal region in a living body. For example, the lesion may be inflammation or a bleeding region.

The illumination light having the first illumination property includes light in a first group in the first determination mode, and the light is at least one of a plurality of colors of light. The illumination light having the second illumination property includes light in a second group in the second determination mode, and the light is at least one of the plurality of colors of light and is different from the light in the first group.

As a result, the spectral characteristic of the illumination light in the first determination mode and the spectral characteristic of the illumination light in the second determination mode can be made different. Thus, the support information can be generated using the illumination light having the optimum spectral characteristic in each determination mode. The group may include only one color of light. The light in the first group and the light in the second group only need to be partly different, and may have an overlapping portion. For example, in the examples in FIGS. 2 and 4, the first group includes the light A and V and the second group includes the light V and G. In these examples, the light V overlaps, however, combinations of colors are different.

Furthermore, according to the present embodiment, the plurality of colors of light include the violet light, the amber light, and the green light.

As a result, information on the blood vessel in the surface layer of the mucosa can be acquired using the violet light or the green light, and the support information can be extracted from this information. Compared with the green light, the violet light is used to acquire information on the blood vessel at a shallower part. The amber light can be used to acquire information on the blood vessel in the deep layer of the mucosa or information on a hemoglobin concentration at a puddle of blood or the like, and the support information can be extracted from the information.

Furthermore, according to the present embodiment, the determination mode is the presence diagnosis mode for diagnosing the presence of the lesion candidate included in the object, or the qualitative diagnosis mode for diagnosing the status of the lesion candidate. Alternatively, the determination mode may be the treatment support mode for supporting the treatment. The treatment support mode will be described later in another embodiment.

The illumination light in the qualitative diagnosis mode includes light that is not included in the illumination light in the presence diagnosis mode and is used for observing the inflammation, the blood vessel in an intermediate layer, or the blood vessel in the deep layer. This illumination light includes light having a wavelength longer than that of the light in the illumination light in the presence diagnosis mode. Specifically, the illumination light in the presence diagnosis mode includes the violet light and the amber light. The illumination light in the qualitative diagnosis mode includes the violet light and the green light. Alternatively, as will be described later in another embodiment, the illumination light in the qualitative diagnosis mode may include the green light, the amber light, and the red light, or illumination light for distance measurement.

As a result, using the violet light or the green light allows imaging of the blood vessel in the surface layer of the mucosa in good contrast. Further, using the amber light allows imaging of the blood vessel in the deep part of the mucosa, the light and shade of the blood in the bleeding region, or the like in good contrast. Using the violet light and the amber light in the presence diagnosis mode allows extraction of various types of lesion candidate. Further, combining the violet light and the green light in the qualitative diagnosis mode allows acquisition of the support information in accordance with the NBI diagnosis. Further, combining the green light, the amber light, and the red light in the qualitative diagnosis mode allows acquisition of the support information on inflammatory diseases such as ulcerative colitis from the information on the blood vessel in the surface layer and the blood vessel in the deep layer. Still further, using the illumination light for distance measurement in the qualitative diagnosis mode allows acquisition of the support information on the status of the mucosa or the lesion such as cancer from the information on a shape or structure of the mucosa.

As will be described later in another embodiment, the illumination light in the treatment support mode may include light used for extracting the range of the lesion or a bleeding point in the generation process of the support information. Specifically, the illumination light in the treatment support mode may include the violet light and amber light that are the narrow band light, and the illumination light for distance measurement. Alternatively, the illumination light in the treatment support mode may include the red light, and the amber light that is the narrow band light.

Combining the violet light, the amber light, and the illumination light for distance measurement in the treatment support mode allows extraction of the range of the lesion as the support information from the information on the blood vessel in the surface layer and the blood vessel in the deep layer and the information on the shape or structure of the mucosa. As a result, the range of the lesion can be presented to the physician or surgeon, and thus the treatment such as ablation of the lesion can be supported. Further, combining the red light and the amber light in the treatment support mode allows acquisition of the information on the bleeding point in the puddle of blood or the like from the information on the light and shade of hemoglobin.

Furthermore, according to the present embodiment, the endoscope apparatus 10 includes the display section 300 that displays the display image. The illumination source section 140 emits the display illumination light used for generating the display image and the support illumination light different from the display illumination light in the illumination property in a time-division manner. The processing section 110 generates the display image based on the image signal acquired when the display illumination light is emitted. The processing section 110 generates the support information based on the image signal acquired when the support illumination light is emitted. Then, the processing section 110 performs the image processing for adding the display content based on the support information to the display image.

Since the support illumination light is optimized for the inference process by the AI, it may not be suitable for observation. In the present embodiment, the display image is captured using the display illumination light different from the support illumination light, and thus the display image suitable for observation can be presented to the physician or surgeon. Furthermore, according to the present embodiment, the display content corresponding to the support information is displayed on the display section 300 based on the support information generated by the support information generation section 121. Since the illumination property is optimized in accordance with the observation purpose, the highly accurate support information generated from the image captured using the illumination light can be presented to the physician or surgeon to support the diagnosis or treatment.

Furthermore, according to the present embodiment, the display content based on the support information is at least one of the position and contour of a target portion indicated by the support information.

As a result, at least one of the position and contour of the target portion detected by the support information generation section 121 can be displayed on the display section 300. For example, displaying at least one of the position and contour on the display section 300 in the presence diagnosis mode allows presentation of the presence of the lesion candidate to the physician or surgeon.

Furthermore, according to the present embodiment, the processing section 110 generates the first support information when the illumination property of the support illumination light is the first illumination property, and performs the image processing for adding first display content to the display image based on the first support information. The processing section 110 switches the illumination property of the support illumination light to the second illumination property based on the first support information, and generates the second support information. The processing section 110 performs the image processing for adding second display content different from the first display content to the display image based on the second support information.

As a result, the highly accurate support information acquired using the illumination light having the optimum illumination property can be displayed on the display image captured using the display illumination light. Furthermore, the support information with different content for each illumination property can be acquired to be displayed on the display image. As a result, various types of support information in accordance with the observation purpose can be superimposed on the display image suitable for observation so as to be presented to the physician or surgeon.

Furthermore, according to the present embodiment, the display illumination light is white light. The support illumination light includes at least one of the violet light, amber light, and green light.

As a result, a white light image can be displayed on the display section 300 as the display image, and the support information can be added to the white light image to be presented to the physician or surgeon. Further, since the support illumination light includes at least one of the violet light, amber light, and green light, the illumination property suitable for the observation purpose can be implemented. That is, using the violet light or the green light allows imaging of the blood vessel in the surface layer of the mucosa in good contrast. Using the amber light allows imaging of the blood vessel in the deep part of the mucosa, the light and shade of the blood in the bleeding region, or the like in good contrast. Alternatively, these types of light may be combined in accordance with the observation purpose. For example, in order to acquire the support information in accordance with the NBI diagnosis, the violet light and the green light may be combined.

Furthermore, according to the present embodiment, the endoscope apparatus 10 includes the storage section 160 that stores the information on the trained model. The trained model is a model that has learned to output the support information in response to the image signal. The processing section 110 generates the support information from the image signal by the processing based on the trained model.

As a result, the support information can be generated from the image signal through the inference process by the AI. The trained model has learned with the training data made by the expert such as the physician or surgeon, so that the trained model reflecting the knowledge of the expert can be generated. With such a trained model, the support information based on the knowledge of the expert can be provided to the user of the endoscope apparatus 10.

As described above, the trained model can include the neural network. As for the neural network, any of known various types of AI technology may be adopted. In order to use the neural network, it is necessary to develop software for implementing the learning or the inference algorithm. However, since several software packages are now in stores or released for free, these packages may be used. The algorithm of the machine learning for the neural network may be any of known various learning algorithms, and may be a supervised learning algorithm using an error inverse propagation method, for example.

Furthermore, according to the present embodiment, the storage section 160 stores information on a first trained model and a second trained model. The first trained model is a trained model that has learned to output the first support information in response to the image signal acquired when the illumination property is the first illumination property. The second trained model is a trained model that has learned to output the second support information in response to the image signal acquired when the illumination property is the second illumination property. The processing section 110 generates the first support information by the processing based on the first trained model when the illumination property is the first illumination property. The processing section 110 generates the second support information by the processing based on the second trained model when the illumination property is the second illumination property.

According to the present embodiment, the trained model corresponding to each illumination property is prepared, so that the support information can be generated using the trained model suitable for the observation purpose. That is, not only the illumination property but also the AI is optimized in accordance with the observation purpose. As a result, the highly accurate support information in accordance with the observation purpose can be presented to the physician or surgeon.

Functions and operation of the endoscope apparatus 10 described above may be implemented by a program. That is, a program describing the functions and operation of the endoscope apparatus 10 may be stored in a memory, and the program may be executed by a computer to implement the functions and operation of the endoscope apparatus 10. The computer is a device including an input device, a processing section, a storage section, and an output section, and is an information processing device such as a PC. The program causes the computer to implement steps of generating the first support information based on the image signal acquired when the illumination property is the first illumination property, switching the illumination property to the second illumination property based on the first support information, and generating the second support information based on the image signal acquired when the illumination property is the second illumination property.

Furthermore, the program of the present embodiment may be stored in an information storage medium. The information storage medium is a computer-readable medium. The information storage medium may be any of various storage media including an optical disk such as a DVD or a CD, a hard disk drive, or a semiconductor memory such as a nonvolatile memory or a ROM. The computer performs various processes according to the present embodiment based on the program and data stored in the information storage medium. That is, the information storage medium stores the program causing the computer to function as the endoscope apparatus 10 according to the present embodiment.

3. Second Embodiment

In a second embodiment, the qualitative diagnosis mode is a UC inflammation diagnosis mode. UC represents ulcerative colitis. The switching method from the presence diagnosis mode to the qualitative diagnosis mode is the same as that in the first embodiment, and thus the UC inflammation diagnosis mode is described below.

FIG. 9 is a diagram illustrating the light emission sequence and the imaging sequence in the UC inflammation diagnosis mode. Description that is common to that of FIG. 2 or the like is omitted.

The illumination source control section 151 causes the illumination source section 140 to emit the white light in the period TE. In the UC inflammation diagnosis mode, the support illumination light includes the red light R, the green light G, and the amber light A. The illumination source control section 151 causes the illumination source section 140 to emit the red right R and the green light G in the period TAI1, and the amber light A in the period TAI2. The periods TE, TAI1, and TAI2 are repeated to emit the illumination light described above in a time-division manner. The red light R and the amber light A both belong to a red region, and pass through a red filter in a primary color imager adopting a Bayer filter, for example. Accordingly, the red light R and the amber light A are emitted in a time-division manner. The red light R and the amber light A may be emitted in reverse order.

The combination of the red light R, green light G, and amber light A makes the illumination light suitable for imaging the blood vessel in the deep layer of the mucosa. The qualitative support information in the UC inflammation diagnosis mode is a diagnosis result or a classification result based on the visibility of the blood vessel in the deep layer. The term "visibility" does not mean that a person actually sees the blood vessel, but means a contrast of the blood vessel in the deep layer in the image, for example. For example, the support information generation section 121 generates the support information that is an inflammation degree that expresses the contrast of the blood vessel in the deep layer by a numerical value.

Figure 10:
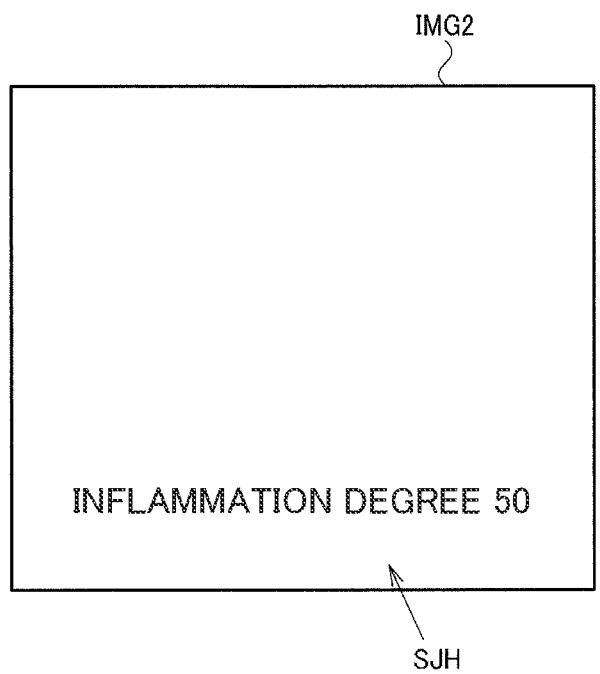
FIG. 10 is a display example of support information in the UC inflammation diagnosis mode.

FIG. 10 is a display example of the support information in the UC inflammation diagnosis mode. The image generation section 111 superimposes information SJH of the inflammation degree generated by the support information generation section 121 on a normal image IMG2 captured using the white light. For example, when the numerical value of the inflammation degree is 50, the image generation section 111 displays the words "Inflammation Degree 50" at a lower part of the normal image IMG2. The numerical value of the inflammation degree varies in accordance with the numerical value determined by the support information generation section 121. The physician or surgeon can diagnose the inflammation degree of the UC by reference to the displayed normal image and numerical value of the inflammation degree.

4. Third Embodiment

In a third embodiment, the treatment support mode can be set. The treatment support mode in the third embodiment is a range diagnosis mode for inferring a range of ablation of the lesion. For example, the range diagnosis mode is selected based on input from the operation section 600. Alternatively, the mode may be switched from the presence diagnosis mode to the range diagnosis mode by a method similar to the method for automatically switching the mode from the presence diagnosis mode to the qualitative diagnosis mode in the first embodiment. Alternatively, the mode may be switched from the qualitative diagnosis mode to the range diagnosis mode. For example, the mode may be switched to the range diagnosis mode when the area of the lesion is determined to be equal to or larger than the predetermined value in the step S6 in FIG. 6.

Figure 11:
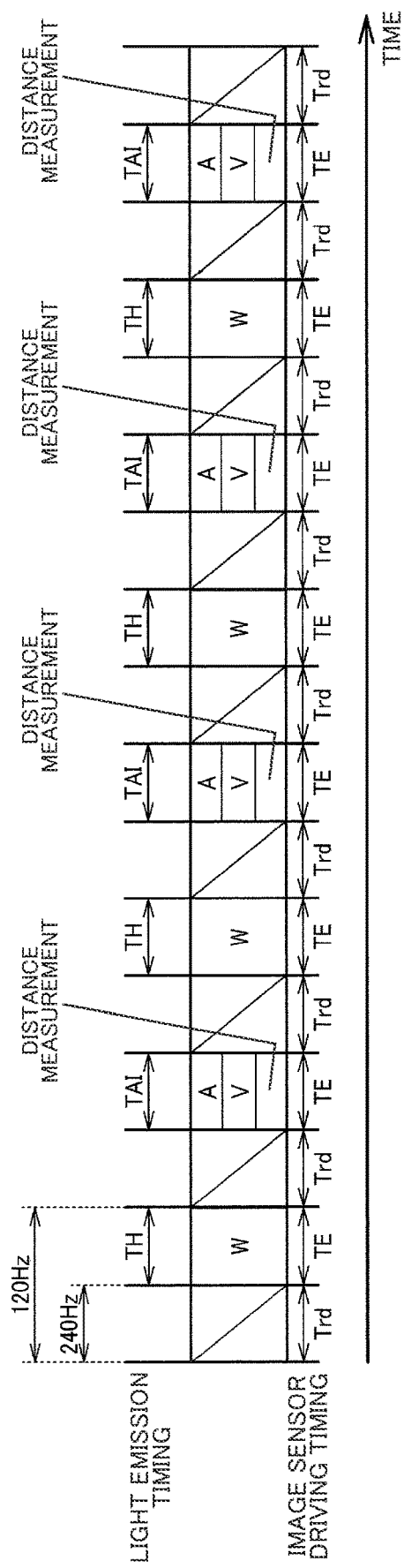
FIG. 11 is a diagram illustrating a light emission sequence and an imaging sequence in a range diagnosis mode.

FIG. 11 is a diagram illustrating the light emission sequence and the imaging sequence in the range diagnosis mode. Description that is common to that of FIG. 2 or the like is omitted.

The illumination source control section 151 causes the illumination source section 140 to emit the amber light A and the violet light V in the period TAI. The processing section 110 measures the distance to the object with the distance measurement sensor 215 in the period TA. That is, the processing section 110 generates the depth map or the like indicating the information on the irregularities of the object surface.

The amber light A and the violet light V of the support illumination light are the same as those of the support illumination light in the presence diagnosis mode. The support information generation section 121 uses a trained model similar to the trained model in the presence diagnosis mode to detect the position or contour of the lesion.

Figure 12:
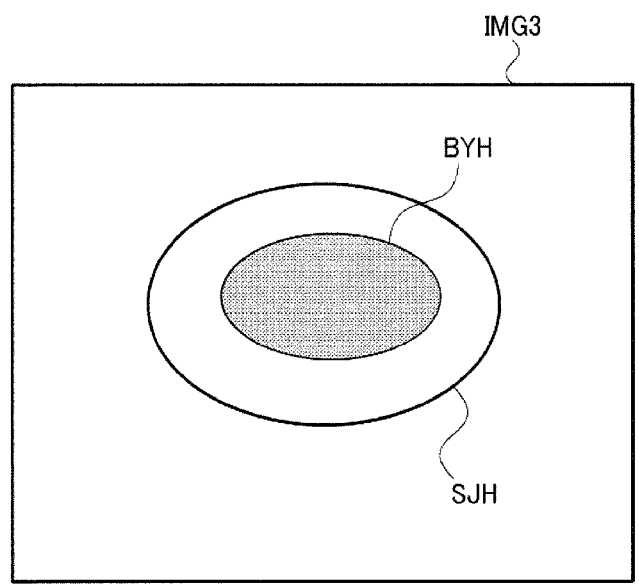
FIG. 12 is an example of a display image in the range diagnosis mode.

FIG. 12 is an example of the display image in the range diagnosis mode. The image generation section 111 displays the position or contour of the lesion BYH detected by the support information generation section 121 on a display image IMG3.

The support information generation section 121 also infers an ablation range SJH of the lesion based on the information on the irregularities of the object surface acquired by the distance measurement and the position or contour of the lesion BYH detected above. The inference is performed based on the trained model that has learned the ablation ranges. That is, the trained model has learned with training data including images of the lesions and annotation information including annotations of the ablation ranges added to the images by the expert such as the physician or surgeon. The image generation section 111 displays the ablation range SJH inferred by the support information generation section 121 on the display image IMG3. As a result, the position or contour of the lesion BYH and the ablation range SJH are displayed on the display image IMG3 as the support information.

The physician or surgeon using the endoscope apparatus 10 can determine the ablation range SJH by reference to the display image IMG3 including the lesion BYH and the ablation range SJH. A method for ablating the lesion by using the endoscope may include endoscopic submucosal dissection (ESD), for example. This method includes marking an outer circumference of the ablation range. The surgeon may refer to the ablation range SJH displayed on the display image IMG3 for marking.

5. Fourth Embodiment

In a fourth embodiment, the treatment support mode is a bleeding point recognition mode for automatically recognizing a bleeding point. The bleeding point recognition mode is used for treatment for stopping bleeding. For example, the bleeding point recognition mode is selected based on input from the operation section 600. Alternatively, the mode may be automatically switched from the presence diagnosis mode to the bleeding point recognition mode. For example, the trained model used in the presence diagnosis mode has further learned with images including bleeding regions such as a puddle of blood or the like. When the submucosa is dissected in the ESD described above, a puddle of blood is created in a recessed portion made after the dissection. The trained model may have learned with training data including such images. Accordingly, the mode may be automatically switched from the presence diagnosis mode to the bleeding point recognition mode when the puddle of blood is created in the image in the ESD.

Figure 13:
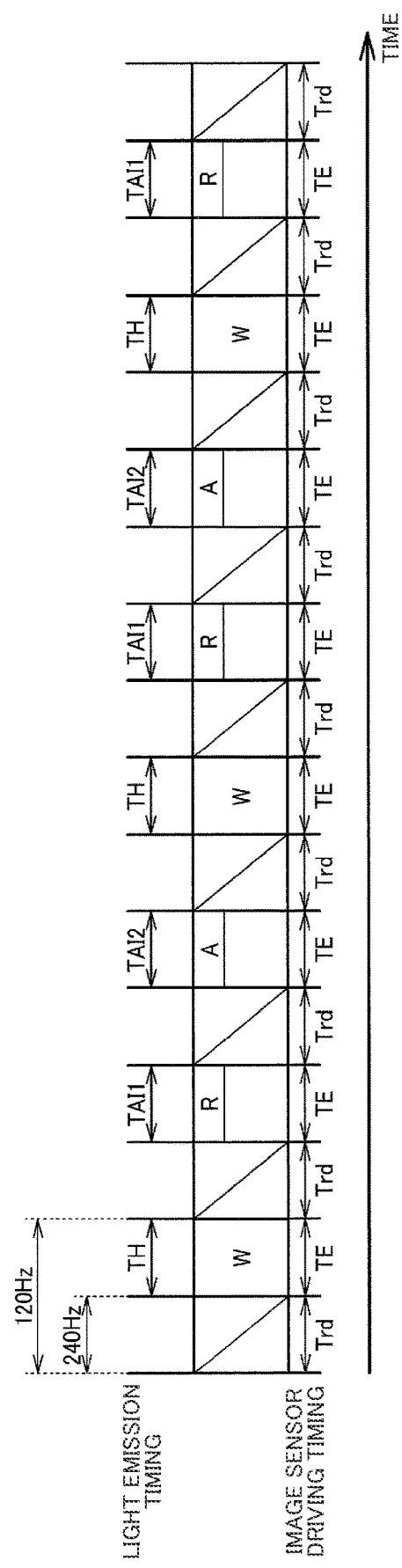
FIG. 13 is a diagram illustrating a light emission sequence and an imaging sequence in a bleeding point recognition mode.

FIG. 13 is a diagram illustrating the light emission sequence and the imaging sequence in the bleeding point recognition mode. Description that is common to that of FIG. 2 or the like is omitted.

The illumination source control section 151 causes the illumination source section 140 to emit the red right R in the period TAI1, and the amber light A in the period TAI2. The red light R and the amber light A may be emitted in reverse order.

Figure 14:
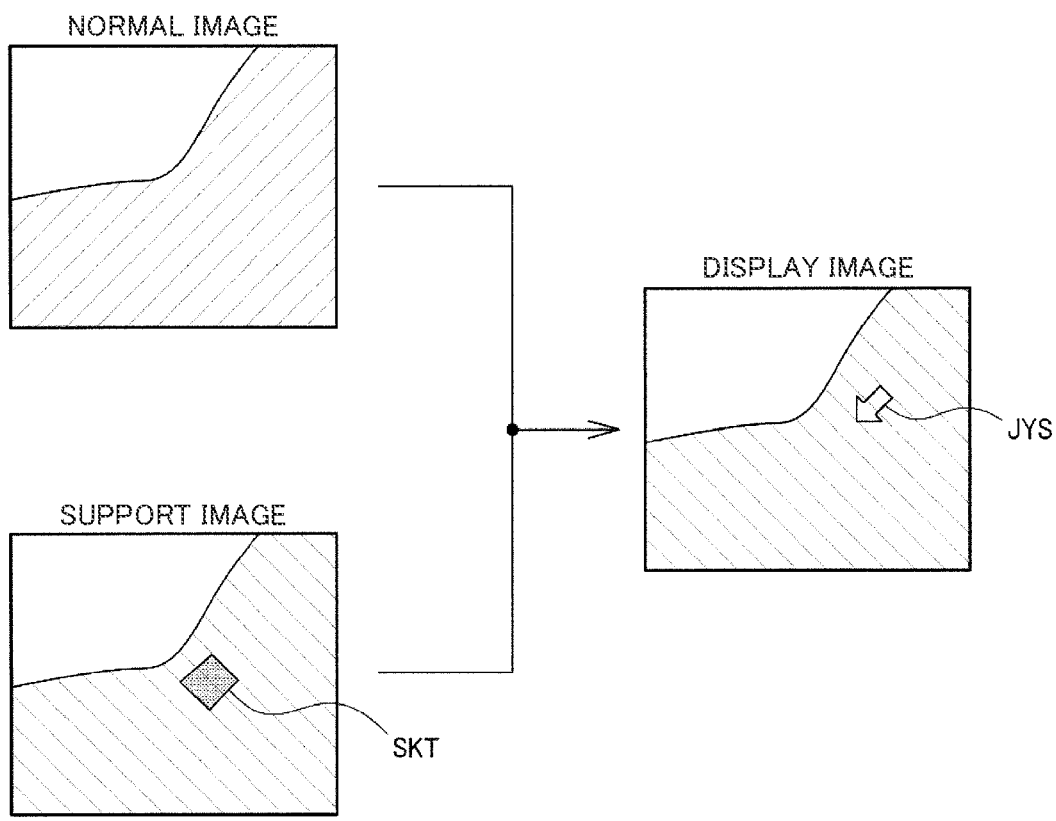
FIG. 14 is an example of a display image in the bleeding point recognition mode.

FIG. 14 is an example of the display image in the bleeding point recognition mode. The puddle of blood appears red or dark red in the normal image of the white light image. A hatched part represents the puddle of blood. The bleeding point exists at the bottom of the puddle of blood. When the blood is mixed with water sent through the air and water supply pipe, the concentration of hemoglobin is high near the bleeding point, however, the contrast of light and shade of hemoglobin is hard to be seen with the white light, and thus the bleeding point is hard to be visually recognized in the normal image.

The puddle of blood appears orange or the like in the support image captured using the red light R and the amber light A. The light in the wavelength region of the red light R is hardly absorbed by hemoglobin, however, the amber light A in the wavelength region around 600 nm is absorbed by hemoglobin to some extent. Thus, the contrast of light and shade of hemoglobin tends to appear in the support image. The concentration of hemoglobin is higher in a bleeding flow from the bleeding point, and this part appears darker orange than circumferential parts. In FIG. 14, SKT represents a darker orange region. The bleeding point can be inferred from the region SKT.

The trained model in the bleeding point recognition mode has learned with training data including images of bleeding regions captured using the red light R and the amber light A and annotation information on bleeding points added to the images by the expert such as the physician or surgeon. The support information generation section 121 uses this trained model to detect the position of the bleeding point from the support image including the puddle of blood and the region SKT described above. The position of the bleeding point is the support information in the bleeding point recognition mode. The image generation section 111 displays the detected position of the bleeding point by an arrow JYS or the like on the display image. The physician or surgeon using the endoscope apparatus 10 can specify the bleeding point by reference to the arrow JYS displayed on the display image.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
an image sensor configured to acquire an image signal;
an illumination source configured to emit illumination light;
a processor comprising hardware, the processor being configured to:
change an illumination property of the illumination light to emit display illumination light and support illumination light;
generate a display image based on the image signal acquired when the display illumination light is emitted, and support information based on the image signal acquired when the support illumination light is emitted;
control the illumination source to emit the display illumination light and the support illumination light in a time-division manner;
generate first support information, which is information on a presence of a lesion candidate, based on the image signal when the illumination property of the support illumination light is a first illumination property;
superimpose first display content based on the first support information on the display image;
switch the illumination property of the support illumination light from the first illumination property to a second illumination property upon determination that the first support information satisfies a predetermined condition;
generate second support information, which is information on a status of the lesion candidate, based on the image signal when the illumination property of the support illumination light is the second illumination property; and
superimpose second display content based on the second support information on the display image;
further comprising a storage device configured to store information on a trained model, wherein the trained model is a model that has learned to output the support information in response to the image signal, and the processor generates the support information from the image signal by processing based on the trained model;
wherein the storage device stores information on a first trained model and a second trained model,
the first trained model is a model that has learned to output the first support information in response to the image signal acquired when the illumination property is the first illumination property,
the second trained model is a model that has learned to output the second support information in response to the image signal acquired when the illumination property is the second illumination property, and
the processor is configured to:
generate the first support information by the processing based on the first trained model when the illumination property is the first illumination property, and
generate the second support information by the processing based on the second trained model when the illumination property is the second illumination property.

2. The endoscope apparatus as defined in claim 1, wherein the processor is configured to:
set the illumination property to the first illumination property to generate the first support information when a determination mode in a generation process of the support information is a first determination mode,
switch the determination mode to a second determination mode based on the first support information, and
set the illumination property to the second illumination property to generate the second support information in the second determination mode.

3. The endoscope apparatus as defined in claim 1, wherein the processor is configured to:
determine whether the first support information satisfies the predetermined condition that an area of the lesion candidate included in the first support information is equal to or larger than a predetermined value, or that an observation magnification of an imaging section is equal to or higher than a predetermined value, and
switch the determination mode from the first determination mode to the second determination mode upon determination that the first support information satisfies the predetermined condition.

4. The endoscope apparatus as defined in claim 1, wherein the lesion candidate is a tumor candidate.

5. The endoscope apparatus as defined in claim 2, wherein
the illumination light having the first illumination property includes light of at least one of a plurality of colors of light in a first group in the first determination mode, and
the illumination light having the second illumination property includes light of at least one of the plurality of colors of light in a second group in the second determination mode, and the light in the second group differs from the light in the first group.

6. The endoscope apparatus as defined in claim 5, wherein the plurality of colors of light include violet light, amber light, and green light.

7. The endoscope apparatus as defined in claim 2, wherein the determination mode is one of a presence diagnosis mode for diagnosing presence of the lesion candidate in an object, a qualitative diagnosis mode for diagnosing status of the lesion candidate, and a treatment support mode for supporting treatment.

8. The endoscope apparatus as defined in claim 7,
wherein the illumination light in the qualitative diagnosis mode includes light that is not included in the illumination light in the presence diagnosis mode, and is used for observing inflammation, a blood vessel in an intermediate layer, and a blood vessel in a deep layer,
wherein the illumination light in the presence diagnosis mode includes violet light and amber light, or
wherein the illumination light in the qualitative diagnosis mode includes the violet light and green light, the green light, the amber light, and red light, or illumination light for distance measurement.

9. The endoscope apparatus as defined in claim 7, wherein
the illumination light in the treatment support mode includes, as light used for extracting a lesion range or a bleeding point in the generation process of the support information,
violet light and amber light that are narrow band light and illumination light for distance measurement, or
red light and the amber light that is the narrow band light.

10. The endoscope apparatus as defined in claim 1, wherein the first display content is at least one of a position and contour of a target portion indicated by the first support information.

11. The endoscope apparatus as defined in claim 1, wherein
the display illumination light is white light, and
the support illumination light includes at least one of violet light, amber light, and green light.

12. A non-transitory information storage medium configured to store a program that causes a computer to:
emit display illumination light and support illumination light in a time-division manner;
generate a display image based on an image signal acquired when the display illumination light is emitted;
generate first support information, which is information on a presence of a lesion candidate, based on an image signal when an illumination property of the support illumination light is a first illumination property;
superimpose first display content based on the first support information on the display image;
switch the illumination property of the support illumination light from the first illumination property to a second illumination property upon determination that the first support information satisfies a predetermined condition;
generate second support information, which is information on a status of the lesion candidate, based on an image signal when the illumination property of the support illumination light is the second illumination property; and
superimpose second display content based on the second support information on the display image;
generate the first support information by processing based on a first trained model when the illumination property is the first illumination property;
switch the illumination property to the second illumination property based on the first support information; and
generate the second support information by processing based on a second trained model when the illumination property is the second illumination property,
wherein the first trained model is a model that has learned to output the first support information in response to the image signal acquired when the illumination property is the first illumination property, and
the second trained model is a model that has learned to output the second support information in response to the image signal acquired when the illumination property is the second illumination property.

13. The endoscope apparatus as defined in claim 1, wherein the illumination property comprises one or more of a spectral characteristic, a light amount, a light distribution characteristic, and a emission timing of the illumination light.

* * * * *